US006916805B2

(12) United States Patent
Dudley et al.

(10) Patent No.: US 6,916,805 B2
(45) Date of Patent: Jul. 12, 2005

(54) QUINOXALINONES AS SERINE PROTEASE INHIBITORS

(75) Inventors: Danette Andrea Dudley, Ann Arbor, MI (US); Jeremy John Edmunds, Ypsilanti, MI (US)

(73) Assignee: Warner-Lambert Company LLC, Morris Plains, NJ (US)

(*) Notice: Subject to any disclaimer, the term of this patent is extended or adjusted under 35 U.S.C. 154(b) by 81 days.

(21) Appl. No.: 10/038,006

(22) Filed: Jan. 4, 2002

(65) Prior Publication Data

US 2002/0086866 A1 Jul. 4, 2002

Related U.S. Application Data

(62) Division of application No. 09/601,606, filed as application No. PCT/US98/26704 on Dec. 15, 1998, now Pat. No. 6,410,536.
(60) Provisional application No. 60/080,042, filed on Mar. 31, 1998.

(51) Int. Cl.$^7$ ...................... A61K 31/551; C07D 234/12
(52) U.S. Cl. ...................... 514/221; 514/183; 540/460; 540/473; 540/504; 540/505; 540/514; 540/517; 540/521
(58) Field of Search .............................. 540/460, 473, 540/505, 504, 514, 517, 521; 514/183, 221

(56) References Cited

U.S. PATENT DOCUMENTS

| | | | |
|---|---|---|---|
| 4,082,735 A | 4/1978 | Jones et al. | 260/112.5 R |
| 4,082,736 A | 4/1978 | Jones et al. | 260/112.5 R |
| 4,870,175 A | 9/1989 | Suzuki et al. | 544/354 |

FOREIGN PATENT DOCUMENTS

| | | |
|---|---|---|
| JP | 63145272 | 6/1988 |
| JP | 63-301874 | 12/1988 |
| JP | 1254348 | 10/1989 |
| WO | 9707116 | 2/1997 |
| WO | 97487006 | 12/1997 |
| WO | 9801428 | 1/1998 |
| WO | WO 98/13368 A1 | 4/1998 |
| WO | 99813368 | 4/1998 |

OTHER PUBLICATIONS

Ittyerah et al., Chemical Abstracts, vol. 52:77247, 1958.*

Stetter, Chemical Abstracts, vol. 48:7118, 1954.*

PCT International Search Report, PCT/US98/26704, 1998.

Lappato et al., "X-ray structure of anistasin at 1.9 Å resolution and its modeled complex with blood coagulation factor Xa", *The EMBO Journal*, vol. 16, No. 17, 5151–5161, 1987.

Mellott et al., "Enhancement of Recombinant Tissue Plasminogen Activator–induced Reperfusion by Recominant Tick Anticoagulant Peptide, A Selective Factor Xa Inhibitor, in a Canine Model of Femoral Arterial Thrombosis", *Fibrinolysis*, 7, 1993, 195–202.

Lynch et al., "Primary Prevention of Coronary Arterial Thrombosis with the Factor Xa Inhibitor rTAP in a Canine Electrolytic Injury Model", *Thrombosis and Haemostasis*, 74 (2) 640–5, 1995.

Schaffer et al., "Antithrombotic Efficacy of Recombinant Tick Anticoagulant Peptide", *Circulation*, 1991, 84:1741–1748.

Fioravanti, et al., "Antithrombotic Activity of Recombinant Tick Anticoagulant Peptide and Heparin in a Rabbit Model of Venous Thrombosis", *Thrombosis Research*, 71, 317–324, 1993.

Wong et al., "Antithrombotic Actions of Selective Inhibitors of Blood Coagulation Factor Xa in Rat Models of Thrombosis", *Thrombosis Research*, vol. 83, No. 2, 117–126, 1996.

Edmunds and Rapundalo, *Annual Reports in Medicinal Chemistry*, 31, 51–60, 1996.

Kunitada and Nagahura, "Factor Xa Inhibitors", *Current Pharmaceutical Design*, 1996, 2, 531–542.

Matuszczak and Mereiter, "Syntheses in the series of pyrazolyl–substituted quinoxalines", *Heterocycles*, vol. 45, No. 12, 1997, 2449–2462.

Leardini et al., "Peroxydicarbonate–Mediated Oxidation of N–(ortho–Aryloxyphenyl) and N–(ortho–Arylaminophyenl)aldimines", *Tetrahedron*, vol. 51, No. 44, 12143–12158, 1995.

Awad and Hassan, "Studies in Vilsmeier–Haack Reaction. Application to Quinoxalinones", *Collect. Czech. Chem. Commun.*, vol. 55, 1990, 2715–2721.

Otomasu et al., "Quinoxaline 1,2–Dihydroimidazo[1,2–a]–quinoxaline 1,2–Dihyro–3H–pyrimido[1,2–a]quinoxaline", *Yakugaku Zasshi*, 90 (11), 1391–1395, 1970.

Seth et al., "Studies in Antiamoebic Agents: Synthesis of Substituted Inophenazines, Azaindophenazines & Azaquinoxalines", *Indian Journal of Chemistry*, vol. 12, 1974, 124–128.

(Continued)

Primary Examiner—Richard L. Raymond
(74) *Attorney, Agent, or Firm*—Cynthia M. Bott; Andrew J. Leon; Heidi M. Berven

(57) ABSTRACT

This invention discloses quinoxalinones which display inhibitory effects on serine proteases such as factor Xa, thrombin, and/or factor VIIa. The invention also discloses pharmaceutically acceptable salts and prodrugs of the compounds, pharmaceutically acceptable compositions comprising the compounds, their salts or prodrugs, and methods of using them as therapeutic agents for treating or preventing disease states in mammals characterized by abnormal thrombosis.

18 Claims, No Drawings

OTHER PUBLICATIONS

Sparatore et al., "Quinolizidine Derivatives as Potential Antitumoral Agents", *Il Farmaco*, 44 (10), 945–950, 1989.

Hahn et al., "Effect of Mepyramine and Spasmolytic Agnets on Guinea–Pig Anaphylaxis with Special Reference to the Protracted Shock", *Arch. Int. Pharmacodyn.*, 199, 108–121, 1972.

Chemical Abstracts, vol. 111, No. 9, 1989, abstract 78027u.

Morrow and Regan, "Some Unusual Oxidation Reactions of 1,3–Diaryl–3,4–dihydro–7–methoxy–2(1H)–quinoxalineones", *J. Org. Chem.*, vol. 36, No. 1, 1971, 27–31.

Katoh et al., "Structural Analysis of N–( –phenylalkyl)substituted quinoxaline–2(1H)–ones and –thiones", *Heterocycles*, vol. 44, No. 1, 1997, 357–366.

Kurasawa et al., "Revised Structure for the Production from the Reaction of 3–Hydrazinocarbonylmethylene–2–oxo–1,2,3,4–tetrahydroquinoxaline with Nitrous Acid", *Chem. Pharm. Bull.*, 32 (10), 4140–4143, 1984.

JP63301874, Dec. 8, 1998, Ito Yoshikuni et al., IPC Classifications, C07D241/44 Abstract, 1988.

* cited by examiner

QUINOXALINONES AS SERINE PROTEASE INHIBITORS

CROSS REFERENCE TO RELATED APPLICATIONS

This application is a divisional of U.S. Ser. No. 09/601,606 filed Aug. 3, 2000, now U.S. Pat. No. 6,410,536, which is a 371 filing of PCT/US98/26704 filed Dec. 15, 1998, having benefit of Provisional Application No. 60/080,042 filed Mar. 31, 1998.

FIELD OF THE INVENTION

In one aspect, this invention discloses quinoxalinones which display inhibitory effects on serine proteases such as factor Xa, thrombin, and/or factor VIIa. The invention also discloses pharmaceutically acceptable salts and prodrugs of the compounds, pharmaceutically acceptable compositions comprising the compounds, their salts or prodrugs, and methods of using them as therapeutic agents for treating or preventing disease states in mammals characterized by abnormal thrombosis.

BACKGROUND OF THE INVENTION

In economically developed countries, cardiovascular disease still represents a major cause of mortality. In particular, abnormal coagulation and inappropriate thrombus formation within blood vessels precipitates many acute cardiovascular disease states. While it has long been recognized that a variety of plasma proteins such as fibrinogen, serine proteases, and cellular receptors are involved in hemostasis, it is the abnormal regulation that has emerged as important contributing factors to cardiovascular disease. Thrombin can be considered the key or principal regulatory enzyme in the coagulation cascade; it serves a pluralistic role as both a positive and negative feedback regulator in normal hemostasis. However, in some pathologic conditions, the former is amplified through catalytic activation of cofactors required for thrombin generation such as factor Xa. Factor Xa, as part of the prothrombinase complex composed of non-enzymatic cofactor Va, calcium ions, and a phospholipid membrane surface regulates the generation of thrombin from its zymogen prothrombin. Furthermore, the location of the prothrombinase complex at the convergence of both the intrinsic and extrinsic coagulation pathways suggests that inhibition of factor Xa, and hence thrombin generation, may be a viable approach to limiting the procoagulant activity of thrombin.

Indeed, ample evidence exists for the role of factor Xa inhibitors as anticoagulants. Antistasin, a potent inhibitor of blood coagulation factor Xa from the Mexican leech: *Haementeria officinalis*, displays antithrombotic activity in various models of arterial and venous thrombosis (Lapatto et al., *Embo. J.*, 1997:5151–5161). Other protein or polypeptide factor Xa inhibitors include recombinant tick anticoagulant peptide (rTAP), which is known to accelerate the recombinant tissue plasminogen activator mediated clot lysis and prevent acute reocclusion in the dog, hence indicating factor Xa inhibitors may be useful as an adjunct to thrombolytic therapy (Mellott et al., *Fibrinolysis*, 1993:195–202). Furthermore, in a canine coronary artery electrolytic lesion model, rTAP was demonstrated to reduce thrombus mass and time to occlusion in the absence of dramatic hemodynamic or hemostatic changes indicating the primary role for factor Xa in the process of arterial thrombosis (Lynch et al., *Thromb. Haemostasis*, 1995:640–645; Schaffer et al., *Circulation*, 1991:1741–1748). On the venous side, rTAP was also demonstrated to reduce fibrin deposition in a rabbit model of venous thrombosis while having little affect on systemic hemostatic parameters (Fioravanti et al., *Thromb. Res.*, 1993:317–324). In addition to these relatively high molecular weight proteins that are not suitable as oral antithrombotic agents, there also exist examples of low molecular weight factor Xa inhibitors. In particular, DX9065a, a low molecular weight synthetic factor Xa inhibitor, has also shown antithrombotic potential in various experimental thrombosis rat models. In both arteriovenous shunt and venous stasis models, inhibition of thrombus formation was achieved at doses that had little effect on APTT, indicating that DX9065a is effective in preventing thrombosis and hence has therapeutic antithrombotic potential (Wong et al., *Thromb. Res.*, 1996:117–126).

The majority of factor Xa inhibitors known to date have been previously summarized in two reviews (Edmunds et al., *Annual Reports in Medicinal Chemistry*, 1996:51 and Kunitada and Nagahara, *Curr. Pharm. Des.*, 1996:531–542). However, it is readily apparent that there still exists a need for more effective agents that regulate factor Xa proteolytic activity.

Some quinoxalinones have been reported, and these compounds have displayed marked pharmacological activity: Japanese Application: JP 88-99097 880421; Japanese Application: JP 89-254348 890929; CAN 116: 83686; World Publication 9707116; Otomasu et al., *Yakugaku Zasshi*, 1970;90(11):1391–1395; Seth M et al., *Indian J. Chem.*, 1974;12(2):124–1288; Japanese Patent 63145272; Sparatore et al., *Farmaco*, 1989;44(10):945–950; and F. Hahn et al., *Arch. Int. Pharmacodyn. Ther.*, 1992:108.

None of the above articles set forth above disclose or suggest compounds of Formula I that are inhibitors of serine proteases involved in the blood coagulation cascade.

SUMMARY OF THE INVENTION

One object of the present invention is to provide serine protease inhibitors that display inhibitory activity towards enzymes involved in the coagulation cascade and principally the target enzymes, factor Xa, thrombin, and factor VIIa.

A further object of the present invention is to provide serine protease inhibitors that display inhibitory activity towards the target enzyme factor Xa and are provided for in a pharmacologically acceptable state.

Still, a further object of the present invention is to provide for the use of these factor Xa inhibitors and formulations thereof as anticoagulant and factor Xa inhibitory agents.

Yet, a further object of the present invention is to provide for the use of these factor Xa inhibitors and formulations thereof for therapeutic treatment of various thrombotic maladies.

A further object of the present invention is a process for the synthesis of these low molecular weight thrombin inhibitors. The enzyme inhibitors of the present invention are encompassed by the structure of general Formula I set forth below.

The present invention meets these objectives and provides for novel compounds that display antithrombotic activity. More specifically, the present invention provides for novel compounds that display antithrombotic activity via the inhibition of factor Xa as reflected in Formula I, or pharmaceutically acceptable salts or prodrug forms thereof. The present invention also provides pharmaceutically acceptable compositions comprising the novel compounds or their salts or prodrug forms, and methods of using them as therapeutic agents for treating or preventing disease states in mammals characterized by abnormal thrombosis.

Thus in a first embodiment, the present invention provides novel compounds of Formula I:

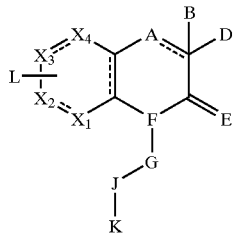

I or stereoisomers or pharmaceutically acceptable salts, esters, amides or prodrugs thereof, wherein:

A is selected from N, Nalkyl, NCH$_2$, N(alkyl)CH$_2$, CH$_2$N, CH$_2$N(alkyl), NO;

B is selected from H, (C$_{3-20}$)alkyl, cycloalkyl, heteroalkyl, cycloalkylalkyl, heteroalkylalkyl, aryl, arylalkyl, heterocycle, heterocycloalkyl, each optionally substituted with R$_1$ and R$_2$;

D is selected from H, (C$_{3-20}$)alkyl, cycloalkyl, heteroalkyl, cycloalkylalkyl, heteroalkylalkyl, aryl, arylalkyl, heterocycle, heterocycloalkyl, each optionally substituted with R$_1$ and R$_2$;

E is absent or selected from O, S, NH;

F is selected from N, NCH$_2$, CH$_2$N;

G is absent or selected from alkyl, alkyl interrupted by one or more heteroatoms, cycloalkyl, cycloalkyl interrupted by one or more heteroatoms;

J is absent or selected from aryl or heterocycle each optionally substituted with R$_1$ and R$_2$;

K is absent or selected from an alkyl, alkyl interrupted by one or more heteroatoms, cycloalkyl interrupted by one or more heteroatoms, cycloalkylalkyl interrupted by one or more heteroatoms, each optionally substituted with R$_1$ and R$_2$;

L is selected from H, chlorine, fluorine, bromine, iodine, OH, O(alkyl), amine, alkyl, fluoroalkyl, amide, NO$_2$, SH, S(O)$_n$(alkyl), SO$_3$H, SO$_3$alkyl, aldehyde, ketone, acid, ester, urea, Oalkylamide, Oalkylester, Oalkylacid, Nalkylacid, alkylamine, alkylamide, alkylketone, alkylacid, alkylester, alkylurea, Nalkylamide, Nalkylester, NC(=O)alkyl, NC(=O)aryl, nitrile, NC(=O)cycloalkyl, NC(=O)cycloalkylalkyl, NC(=O)alkylaryl, R$_1$, R$_2$;

R$_1$ is selected from H, amine, alkylamine, amide, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, C(=NH)alkyl, alkylC(=NH)alkyl, C(=NR$_3$)N(R$_4$)(R$_5$), alkylC(=NR$_3$)N(R$_4$)(R$_5$);

R$_2$ is selected from H, chlorine, fluorine, bromine, iodine, OH, Oalkyl, amine, alkylaldehyde, alkylamide, alkylester, alkylketone, alkylacid, Oalkylamide, Oalkylacid, Oalkylester, aninealkylacid, aminealkylamide, aminealkylester, NC(=O)alkyl, NC(=O)aryl, NC(=O)cycloalkyl, NC(=O)alkylaryl, alkylamine, amide, aldehyde, ester, ketone, NO$_2$, SH, S(O)$_n$(C$_{1-10}$alkyl), SO$_3$H, SO$_3$alkyl, CHO, acid, alkyl, C(=NH)alkyl, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, alkylC(=NH)alkyl, C(=NR$_3$)N(R$_4$)(R$_5$), alkylC(=NR$_3$)N(R$_4$)(R$_5$);

R$_3$, R$_4$, and R$_5$ are a hydrogen atom, alkyl group having 1 to 4 carbon atoms optionally interrupted by a heteroatom, or R$_4$ and R$_5$ are bonded to form —(CH$_2$)$_p$—W—(CH$_2$)$_q$—, wherein p and q are an integer of 2 or 3, a certain position on the methylene chain is unsubstituted or substituted by an alkyl group having 1 to 4 carbon atoms, W is a direct bond, —CH$_2$—, —O—, —N(R$_6$)—, or —S(O)$_r$— wherein R$_6$ is H or alkyl, and r is 0 or 1 or 2;

n is selected from 0, 1, 2;

X$_1$ is C or N;

X$_2$ is C or N;

X$_3$ is C or N;

X$_4$ is C or N; and

--- represents an optional additional bond when A is N.

Preferred compounds according to this invention have the Formula II:

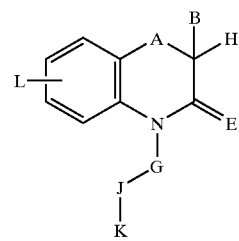

II or stereoisomers or pharmaceutically acceptable salts, esters, amides, or prodrugs thereof, wherein A, B, E, G, J, K, and L are as defined above.

Another preferred group of compounds have the Formula III:

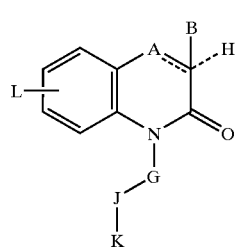

III or stereoisomers or pharmaceutically acceptable salts, esters, amides, or prodrugs thereof, wherein A is N or Nalkyl, and B, G, J, K, L, and --- are as defined above.

Even more preferred compounds have the Formula IV:

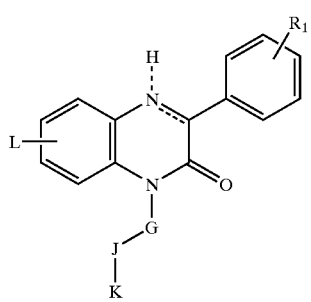

IV or stereoisomers or pharmaceutically acceptable salts, esters, amides, or prodrugs thereof, wherein G, J, K, L, R$_1$, and --- are as defined above.

The most preferred compounds provided by this invention are compounds of Formula V:

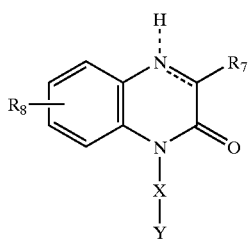

or stereoisomers or pharmaceutically acceptable salts, esters, amides, or prodrugs thereof, wherein X, Y, $R_7$, $R_8$, and --- are as follows:

X is selected from $(CH_2)_5$,
$(CH_2)_4$,
$(CH_2)_6$,
$CH_2C(=O)NHCH_2CH_2$,
$CH_2CH_2NHC(=O)CH_2$,
$(CH_2)_2NH(CH_2)_2$,
$(CH_2)_2O(CH_2)_2$,
$C_6H_4$,
$CH_2C_6H_4$,
$C_6H_4CH_2$,
$C_6H_{10}$,
$CH_2C_6H_{10}$,
$C_6H_{10}CH_2$,
$C_5H_8$,
$CH_2C_5H_8$,
$C_5H_8CH_2$, and
$CH_2CH=CHCH_2CH_2$;

Y is selected from 2,6-dimethylpiperidinyl,
piperidinyl,
2,2,6,6-tetramethyl-piperidinyl-4-one,
(2-carboxy)piperidinyl,
(3-carboxy)piperidinyl,
(4-carboxy)piperidinyl,
3,5-dimethylpiperidinyl,
(4-hydroxy)piperidinyl,
(2-imino)piperidinyl,
piperidin-4-one-yl,
(2-dimethylaminomethyl)-piperidinyl,
(4-dimethylamino)-piperidinyl,
(4-sulphonyloxy)-piperidinyl,
(2-phenyl)piperidinyl,
2,5-dimethylpyrrolidinyl,
pyrrolidinyl,
(2-carboxy)pyrrolidinyl,
(3-N-acetyl-N-methyl)pyrrolidinyl,
(3-amino)pyrrolidinyl,
(2,5-bis-methoxymethyl)-pyrrolidinyl,
2-hydroxymethyl-pyrrolidinyl,
2-hydroxymethyl-5-methyl-pyrrolidinyl,
diisopropylamino,
dimethylamino,
diethylamino,
methylamino,
1-methyl-4,5-dihydro-1H-imidazol-2-yl,
2,5-dimethyl-1H-1-imidazolyl,
morpholinyl,
2,6-dimethylmorpholinyl,
piperazinyl,
2,6-dimethylpiperazinyl,
1H-pyrazolyl,
tetrahydro-1H-pyrazolyl, and
2,5-dimethyltetrahydro-1H-1-pyrazolyl;

$R_7$ is selected from (3-amidino)phenyl,
(3-hydroxy)phenyl,
[3-hydroxylamino(imino)methyl]-phenyl,
[3-hydrazino(imino)methyl]-phenyl,
(3-aminomethyl)phenyl,
(3-amino)phenyl,
(3-methylamino)phenyl,
(3-dimethylamino)phenyl,
(5-amidino-2-hydroxy)phenyl,
(1-amidino)piperid-3-yl,
(1-amidino)pyrrolid-3-yl,
(5-amidino)thien-2-yl,
(5-amidino)furan-2-yl,
(5-amidino)-1,3-oxazol-2-yl,
(2-amidino)-1,3-oxazol-5-yl,
1H-pyrazol-5-yl,
tetrahydro-1H-pyrazol-3-yl,
(1-amidino)tetrahydro-1H-pyrazol-3-yl,
(2-amidino)-1H-imidazol-4-yl,
(2-amino)-1H-imidazol-4-yl,
(5-amidino)-1H-imidazol-2-yl,
(5-amino)-1H-imidazol-2-yl,
pyridin-3-yl,
(4-amino)pyridin-3-yl,
(4-dimethylamino)pyridin-3-yl,
(6-amino)pyridin-2-yl,
(6-amidino)pyridin-2-yl,
(2-amino)pyridin-4-yl,
(2-amidino)pyridin-4-yl,
(2-amidino)pyrimid-4-yl,
(2-amino)pyrimidin-4-yl,
(4-amidino)pyrimid-2-yl,
(4-amino)pyrimidin-2-yl,
(6-amidino)pyrazin-2-yl,
(6-amino)pyrazin-2-yl,
(4-amidino)-1,3,5,-triazin-2-yl,
(4-amino)-1,3,5-triazin-2-yl,
(3-amidino)-1,2,4-triazin-5-yl,
(3-amino)-1,2,4-triazin-5-yl,
(3-amidino)benzyl,
(3-amino)benzyl,
(3-aminomethyl)benzyl,
(1-amidino)piperid-3-ylmethyl,
(1-amidino)pyrrolid-3-ylmethyl,
(5-amidino)thien-2-ylmethyl,
(5-amidino)furan-2-ylmethyl,
(5-amidino)oxazol-2-ylmethyl,
(2-amidino)imidazol-5-ylmethyl,
(5-amidino)imidazol-2-ylmethyl, (6-amidino)pyridin-2-ylmethyl,
(6-amino)pyridin-2-ylmethyl,
(2-amidino)pyrimidin-4-ylmethyl,
(2-amino)pyrimidin-4-ylmethyl,
(4-amidino)pyrimidin-2-ylmethyl,
(4-amino)pyrimidin-2-ylmethyl,
(6-amidino)pyrazin-2-ylmethyl,
(6-amino)pyrazin-2-ylmethyl,
3-aminocyclohexyl,
3-amidinocyclohexyl,
3-aminocyclohexylmethyl,
3-amidinocyclohexylmethyl,
3-aminocyclopentyl,
3-amidinocyclopentyl,
3-aminocyclopentylmethyl, and
3-amidinocyclopentylmethyl; and
$R_8$ is selected from H,
Cl,
F,
SH,
SMe,
$CF_3$,
$CH_3$,
$CO_2H$,
$CO_2Me$,
CN,
C(=NH)$NH_2$,
C(=NH)NHOH,
C(=NH)$NHNH_2$,
C(=O)$NH_2$,
$CH_2$OH,
$CH_2NH_2$,
$NO_2$,
OH,
OMe,
$OCH_2$Ph,
$OCH_2CO_2H$,
$O(CH_2)_2CO_2H$,
$O(CH_2)_3CO_2H$,
$NHCH_2CO_2H$,
$NH(CH_2)_2CO_2H$,
$NH(CH_2)_3CO_2H$,
$OCH_2CH_2OH$,
$OCH_2$(1H-tetrazol-5-yl),
$NH_2$,
NHButyl,
$NMe_2$,
NHPh,
$NHCH_2$Ph,
NHC(=O)Me,
NHC(=O)c-Hexyl,
NHC(=O)$CH_2$c-Hexyl,
NHC(=O)Ph,
NHC(=O)$CH_2$Ph,
NHS(=O)$_2$Me,
NHS(=O)$_2$c-Hexyl,
NHS(=O)$_2CH_2$c-Hexyl,
NHS(=O)$_2$Ph, and
NHS(=O)$_2CH_2$Ph.

In one embodiment of Formula V, Y, $R_7$ and $R_8$ are as defined above and X is $(CH_2)_5$. In another embodiment of Formula V, X, $R_7$ and $R_8$ are as defined above and Y is 2,6-dimethylpiperidinyl. In another embodiment of Formula V, X, Y, and $R_8$ are as defined above and $R_7$ is (5-amidino-2-hydroxy) phenyl. In another embodiment of Formula V, X, Y and $R_7$ are as defined above and $R_8$ is H. In yet another embodiment of Formula V, $R_7$ is as defined above and X is $(CH_2)_5$, Y is 2,6-dimethylpiperidinyl and $R_8$ is H. In yet another embodiment of Formula V, $R_7$ is as defined above and X is $(CH_2)_5$, Y is 2,5-dimethylpyrrolidinyl and $R_8$ is H.

Representative compounds of the present invention include:
3-(4-5-[(2R,6S)-2,6-Dimethyltetrahydro-1(2H)-pyridinyl]pentyl-3-oxo-3,4-dihydro-2-quinoxalinyl)benzenecarboximidamide;
1-5-[(2R,6S)-2,6-Dimethyltetrahydro-1(2H)-pyridinyl]pentyl-3-(3-hydroxyphenyl)-2(1H)-quinoxalinone;
3-(4-5-[(2R,6S)-2,6-Dimethyltetrahydro-1(2H)-pyridinyl]pentyl-3-oxo-3,4-dihydro-2-quinoxalinyl)-N-hydroxybenzenecarboximidamide;
3-(4-5-[(2R,6S)-2,6-Dimethyltetrahydro-1(2H)-pyridinyl]pentyl-3-oxo-3,4-dihydro-2-quinoxalinyl)benzenecarboximidohydrazide;
3-[3-(Aminomethyl)phenyl]-1-5-[(2R,6S)-2,6-dimethyltetrahydro-1(2H)-pyridinyl]pentyl-2(1H)-quinoxalinone;
3-(3-Aminophenyl)-1-5-[(2R,6S)-2,6-dimethyltetrahydro-1(2H)-pyridinyl]pentyl-2(1H)-quinoxalinone;
1-5-[(2R,6S)-2,6-Dimethyltetrahydro-1(2H)-pyridinyl]pentyl-3-[3-(methylamino)phenyl]-2(1H)-quinoxalinone;
3-[3-(Dimethylamino)phenyl]-1-5-[(2R,6S)-2,6-dimethyltetrahydro-1(2H)-pyridinyl]pentyl-2(1H)-quinoxalinone;
3-(4-5-[(2R,6S)-2,6-Dimethyltetrahydro-1(2H)-pyridinyl]pentyl-3-oxo-3,4-dihydro-2-quinoxalinyl)-4-hydroxybenzenecarboximidamide;
3-(4-5-[(2R,6S)-2,6-Dimethyltetrahydro-1(2H)-pyridinyl]pentyl-3-oxo-3,4-dihydro-2-quinoxalinyl)tetrahydro-1(2H)-pyridinecarboximidamide;
3-(4-5-[(2R,6S)-2,6-Dimethyltetrahydro-1(2H)-pyridinyl]pentyl-3-oxo-3,4-dihydro-2-quinoxalinyl)-1-pyrrolidinecarboximidamide;
5-(4-5-[(2R,6S)-2,6-Dimethyltetrahydro-1(2H)-pyridinyl]pentyl-3-oxo-3,4-dihydro-2-quinoxalinyl)-2-thiophenecarboximidamide;
5-(4-5-[(2R,6S)-2,6-Dimethyltetrahydro-1(2H)-pyridinyl]pentyl-3-oxo-3,4-dihydro-2-quinoxalinyl)-2-furancarboximidamide;
2-(4-5-[(2R,6S)-2,6-Dimethyltetrahydro-1(2H)-pyridinyl]pentyl-3-oxo-3,4-dihydro-2-quinoxalinyl)-1,3-oxazole-5-carboximidamide;
5-(4-5-[(2R,6S)-2,6-Dimethyltetrahydro-1(2H)-pyridinyl]pentyl-3-oxo-3,4-dihydro-2-quinoxalinyl)-1,3-oxazole-2-carboximidamide;
1-5-[(2R,6S)-2,6-Dimethyltetrahydro-1(2h)-pyridinyl]pentyl-3-(1H-pyrazol-3-yl)-2(1H)-quinoxalinone;
1-5-[(2R,6S)-2,6-Dimethyltetrahydro-1(2H)-pyridinyl]pentyl-3-tetrahydro-1H-pyrazol-3-yl-2(1H)-quinoxalinone;
3-(4-5-[(2R,6S)-2,6-Dimethyltetrahydro-1(2H)-pyridinyl]pentyl-3-oxo-3,4-dihydro-2-quinoxalinyl)-1-pyrazolidinecarboximidamide;
5-(4-5-[(2R,6S)-2,6-Dimethyltetrahydro-1(2H)-pyridinyl]pentyl-3-oxo-3,4-dihydro-2-quinoxalinyl)-1H-imidazole-2-carboximidamide;

3-(2-Amino-1H-imidazol-5-yl)-1-5-[(2R,6S)-2,6-dimethyltetrahydro-1(2H)-pyridinyl]pentyl-2(1H)-quinoxalinone;

2-(4-5-[(2R,6S)-2,6-Dimethyltetrahydro-1(2H)-pyridinyl]pentyl-3-oxo-3,4-dihydro-2-quinoxalinyl)-1H-imidazole-5-carboximidamide;

3-(5-Amino-1H-imidazol-2-yl)-1-5-[(2R,6S)-2,6-dimethyltetrahydro-1(2H)-pyridinyl]pentyl-2(1H)-quinoxalinone;

1-5-[(2R,6S)-2,6-Dimethyltetrahydro-1(2H)-pyridinyl]pentyl-3-(3-pyridinyl)-2(1H)-quinoxalinone;

3-(6-Amino-3-pyridinyl)-1-5-[(2R,6S)-2,6-dimethyltetrahydro-1(2H)-pyridinyl]pentyl-2(1H)-quinoxalinone;

3-[6-(Dimethylamino)-3-pyridinyl]-1-5-[(2R,6S)-2,6-dimethyltetrahydro-1(2H)-pyridinyl]pentyl-2(1H)-quinoxalinone;

3-(6-Amino-2-pyridinyl)-1-5-[(2R,6S)-2,6-dimethyltetrahydro-1(2H)-pyridinyl]pentyl-2(1H)-quinoxalinone;

6-(4-5-[(2R,6S)-2,6-Dimethyltetrahydro-1(2H)-pyridinyl]pentyl-3-oxo-3,4-dihydro-2-quinoxalinyl)-2-pyridinecarboximidamide;

3-(2-Amino-4-pyridinyl)-1-5-[(2R,6S)-2,6-dimethyltetrahydro-1(2H)-pyridinyl]pentyl-2(1H)-quinoxalinone;

4-(4-5-[(2R,6S)-2,6-Dimethyltetrahydro-1(2H)-pyridinyl]pentyl-3-oxo-3,4-dihydro-2-quinoxalinyl)-2-pyridinecarboximidamide;

4-(4-5-[(2R,6S)-2,6-Dimethyltetrahydro-1(2H)-pyridinyl]pentyl-3-oxo-3,4-dihydro-2-quinoxalinyl)-2-pyrimidinecarboximidamide;

3-(2-Amino-4-pyrimidinyl)-1-5-[(2R,6S)-2,6-dimethyltetrahydro-1(2H)-pyridinyl]pentyl-2(1H)-quinoxalinone;

2-(4-5-[(2R,6S)-2,6-Dimethyltetrahydro-1(2H)-pyridinyl]pentyl-3-oxo-3,4-dihydro-2-quinoxalinyl)-4-pyrimidinecarboximidamide;

3-(4-Amino-2-pyrimidinyl)-1-5-[(2R,6S)-2,6-dimethyltetrahydro-1(2H)-pyridinyl]pentyl-2(1H)-quinoxalinone;

6-(4-5-[(2R,6S)-2,6-Dimethyltetrahydro-1(2H)-pyridinyl]pentyl-3-oxo-3,4-dihydro-2-quinoxalinyl)-2-pyrazinecarboximidamide;

3-(6-Amino-2-pyrazinyl)-1-5-[(2R,6S)-2,6-dimethyltetrahydro-1(2H)-pyridinyl]pentyl-2(1H)-quinoxalinone;

4-(4-5-[(2R,6S)-2,6-Dimethyltetrahydro-1(2H)-pyridinyl]pentyl-3-oxo-3,4-dihydro-2-quinoxalinyl)-1,3,5-triazine-2-carboximidamide;

3-(4-Amino-1,3,5-triazin-2-yl)-1-5-[(2R,6S)-2,6-dimethyltetrahydro-1(2H)-pyridinyl]pentyl-2(1H)-quinoxalinone;

5-(4-5-[(2R,6S)-2,6-Dimethyltetrahydro-1(2H)-pyridinyl]pentyl-3-oxo-3,4-dihydro-2-quinoxalinyl)-1,2,4-triazine-3-carboximidamide;

3-(3-Amino-1,2,4-triazin-5-yl)-1-5-[(2R,6S)-2,6-dimethyltetrahydro-1(2H)-pyridinyl]pentyl-2(1H)-quinoxalinone;

3-[(4-5-[(2R,6S)-2,6-Dimethyltetrahydro-1(2H)-pyridinyl]pentyl-3-oxo-3,4-dihydro-2-quinoxalinyl)methyl]benzenecarboximidamide;

3-(3-Aminobenzyl)-1-5-[(2R,6S)-2,6-dimethyltetrahydro-1(2H)-pyridinyl]pentyl-2(1H)-quinoxalinone;

3-[3-(Aminomethyl)benzyl]-1-5-[(2R,6S)-2,6-dimethyltetrahydro-1(2H)-pyridinyl]pentyl-2(1H)-quinoxalinone;

3-[(4-5-[(2R,6S)-2,6-Dimethyltetrahydro-1(2H)-pyridinyl]pentyl-3-oxo-3,4-dihydro-2-quinoxalinyl)methyl]tetrahydro-1(2H)-pyridinecarboximidamide;

3-[(4-5-[(2R,6S)-2,6-Dimethyltetrahydro-1(2H)-pyridinyl]pentyl-3-oxo-3,4-dihydro-2-quinoxalinyl)methyl]-1-pyrrolidinecarboximidamide;

5-[(4-5-[(2R,6S)-2,6-Dimethyltetrahydro-1(2H)-pyridinyl]pentyl-3-oxo-3,4-dihydro-2-quinoxalinyl)methyl]-2-thiophenecarboximidamide;

5-[(4-5-[(2R,6S)-2,6-Dimethyltetrahydro-1(2H)-pyridinyl]pentyl-3-oxo-3,4-dihydro-2-quinoxalinyl)methyl]-2-furancarboximidamide;

2-[(4-5-[(2R,6S)-2,6-Dimethyltetrahydro-1(2H)-pyridinyl]pentyl-3-oxo-3,4-dihydro-2-quinoxalinyl)methyl]-1,3-oxazole-5-carboximidamide;

5-[(4-5-[(2R,6S)-2,6-Dimethyltetrahydro-1(2H)-pyridinyl]pentyl-3-oxo-3,4-dihydro-2-quinoxalinyl)methyl]-1H-imidazole-2-carboximidamide;

2-[(4-5-[(2R,6S)-2,6-Dimethyltetrahydro-1(2H)-pyridinyl]pentyl-3-oxo-3,4-dihydro-2-quinoxalinyl)methyl]-1H-imidazole-5-carboximidamide;

6-[(4-5-[(2R,6S)-2,6-Dimethyltetrahydro-1(2H)-pyridinyl]pentyl-3-oxo-3,4-dihydro-2-quinoxalinyl)methyl]-2-pyridinecarboximidamide;

3-[(6-Amino-2-pyridinyl)methyl]-1-5-[(2R,6S)-2,6-dimethyltetrahydro-1(2H)-pyridinyl]pentyl-2(1H)-quinoxalinone;

4-[(4-5-[(2R,6S)-2,6-Dimethyltetrahydro-1(2H)-pyridinyl]pentyl-3-oxo-3,4-dihydro-2-quinoxalinyl)methyl]-2-pyrimidinecarboximidamide;

3-[(2-Amino-4-pyrimidinyl)methyl]-1-5-[(2R,6S)-2,6-dimethyltetrahydro-1(2H)-pyridinyl]pentyl-2(1H)-quinoxalinone;

2-[(4-5-[(2R,6S)-2,6-Dimethyltetrahydro-1(2H)-pyridinyl]pentyl-3-oxo-3,4-dihydro-2-quinoxalinyl)methyl]-4-pyrimidinecarboximidamide;

3-[(4-Amino-2-pyrimidinyl)methyl]-1-5-[(2R,6S)-2,6-dimethyltetrahydro-1(2H)-pyridinyl]pentyl-2(1H)-quinoxalinone;

6-[(4-5-[(2R,6S)-2,6-Dimethyltetrahydro-1(2H)-pyridinyl]pentyl-3-oxo-3,4-dihydro-2-quinoxalinyl)methyl]-2-pyrazinecarboximidamide;

3-[(6-Amino-2-pyrazinyl)methyl]-1-5-[(2R,6S)-2,6-dimethyltetrahydro-1(2H)-pyridinyl]pentyl-2(1H)-quinoxalinone;

3-(3-Aminocyclohexyl)-1-5-[(2R,6S)-2,6-dimethyltetrahydro-1(2H)-pyridinyl]pentyl-2(1H)-quinoxalinone;

3-(4-5-[(2R,6S)-2,6-Dimethyltetrahydro-1(2H)-pyridinyl]pentyl-3-oxo-3,4-dihydro-2-quinoxalinyl)cyclohexanecarboximidamide;

3-[(3-Aminocyclohexyl)methyl]-1-5-[(2R,6S)-2,6-dimethyltetrahydro-1(2H)-pyridinyl]pentyl-2(1H)-quinoxalinone;

3-[(4-5-[(2R,6S)-2,6-Dimethyltetrahydro-1(2H)-pyridinyl]pentyl-3-oxo-3,4-dihydro-2-quinoxalinyl)methyl]cyclohexanecarboximidamide;

3-(3-Aminocyclopentyl)-1-5-[(2R,6S)-2,6-dimethyltetrahydro-1(2H)-pyridinyl]pentyl-2(1H)-quinoxalinone;

3-(4-5-[(2R,6S)-2,6-Dimethyltetrahydro-1(2H)-pyridinyl]pentyl-3-oxo-3,4-dihydro-2-quinoxalinyl)cyclopentanecarboximidamide;

3-[(3-Aminocyclopentyl)methyl]-1-5-[(2R,6S)-2,6-dimethyltetrahydro-1(2H)-pyridinyl]pentyl-2(1H)-quinoxalinone;

3-[(4-5-[(2R,6S)-2,6-Dimethyltetrahydro-1(2H)-pyridinyl]pentyl-3-oxo-3,4-dihydro-2-quinoxalinyl)methyl]cyclopentanecarboximidamide;

3-(4-4-[(2R,6S)-2,6-Dimethyltetrahydro-1(2H)-pyridinyl]
butyl-3-oxo-3,4-dihydro-2-quinoxalinyl)
benzenecarboximidamide;

3-(4-6-[(2R,6S)-2,6-Dimethyltetrahydro-1(2H)-pyridinyl]
hexyl-3-oxo-3,4-dihydro-2-quinoxalinyl)
benzenecarboximidamide;

2-[3-3-[Amino(imino)methyl]phenyl-2-oxo-1(2H)-
quinoxalinyl]-N-2-[(2R,6S)-2,6-dimethyltetrahydro-1
(2H)-pyridinyl]ethylacetamide;

3-[3-3-[Amino(imino)methyl]phenyl-2-oxo-1(2H)-
quinoxalinyl]-N-[(2R,6S)-2,6-dimethyltetrahydro-1(2H)-
pyridinyl]methylpropanamide;

3-4-[2-(2-[(2R,6S)-2,6-Dimethyltetrahydro-1(2H)-
pyridinyl]ethylamino)ethyl]-3-oxo-3,4-dihydro-2-
quinoxalinylbenzenecarboximidamide;

3-[4-(2-2-[(2R,6S)-2,6-Dimethyltetrahydro-1(2H)-
pyridinyl]ethoxyethyl)-3-oxo-3,4-dihydro-2-
quinoxalinyl]benzenecarboximidamide;

3-(4-4-[(2R,6S)-2,6-Dimethyltetrahydro-1(2H)-pyridinyl]
phenyl-3-oxo-3,4-dihydro-2-quinoxalinyl)
benzenecarboximidamide;

3-(4-4-[(2R,6S)-2,6-Dimethyltetrahydro-1(2H)-pyridinyl]
benzyl-3-oxo-3,4-dihydro-2-quinoxalinyl)
benzenecarboximidamide;

3-[4-(4-[(2R,6S)-2,6-Dimethyltetrahydro-1(2H)-pyridinyl]
methylphenyl)-3-oxo-3,4-dihydro-2-quinoxalinyl]
benzenecarboximidamide;

3-(4-4-[(2R,6S)-2,6-Dimethyltetrahydro-1(2H)-pyridinyl]
cyclohexyl-3-oxo-3,4-dihydro-2-quinoxalinyl)
benzenecarboximidamide;

3-[4-(4-[(2R,6S)-2,6-Dimethyltetrahydro-1(2H)-pyridinyl]
cyclohexylmethyl)-3-oxo-3,4-dihydro-2-quinoxalinyl]
benzenecarboximidamide;

3-[4-(4-[(2R,6S)-2,6-Dimethyltetrahydro-1(2H)-pyridinyl]
methylcyclohexyl)-3-oxo-3,4-dihydro-2-quinoxalinyl]
benzenecarboximidamide;

3-(4-3-[(2R,6S)-2,6-Dimethyltetrahydro-1(2H)-pyridinyl]
cyclopentyl-3-oxo-3,4-dihydro-2-quinoxalinyl)
benzenecarboximidamide;

3-[4-(3-[(2R,6S)-2,6-Dimethyltetrahydro-1(2H)-pyridinyl]
cyclopentylmethyl)-3-oxo-3,4-dihydro-2-quinoxalinyl]
benzenecarboximidamide;

3-[4-(3-[(2R,6S)-2,6-Dimethyltetrahydro-1(2H)-pyridinyl]
methylcyclopentyl)-3-oxo-3,4-dihydro-2-quinoxalinyl]
benzenecarboximidamide, 3-(4-(E)-5-[(2R,6S)-2,6-Dimethyltetrahydro-1(2H)-
pyridinyl]-2-pentenyl-3-oxo-3,4-dihydro-2-quinoxalinyl)
benzenecarboximidamide;

3-[3-Oxo-4-(5-piperidinopentyl)-3,4-dihydro-2-
quinoxalinyl]benzenecarboximidamide;

3-3-Oxo-4-[5-(2,2,6,6-tetramethylpiperidino)pentyl]-3,4-
dihydro-2-quinoxalinylbenzenecarboximidamide;

1-5-[3-3-[Amino(imino)methyl]phenyl-2-oxo-1(2H)-
quinoxalinyl]pentyl-2-piperidinecarboxylic acid;

1-5-[3-3-[Amino(imino)methyl]phenyl-2-oxo-1(2H)-
quinoxalinyl]pentyl-3-piperidinecarboxylic acid;

1-5-[3-3-[Amino(imino)methyl]phenyl-2-oxo-1(2H)-
quinoxalinyl]pentyl-4-piperidinecarboxylic acid;

3-4-[5-(3,5-Dimethylpiperidino)pentyl]-3-oxo-3,4-dihydro-
2-quinoxalinylbenzenecarboximidamide;

3-4-[5-(4-Hydroxypiperidino)pentyl]-3-oxo-3,4-dihydro-2-
quinoxalinylbenzenecarboximidamide;

3-4-[5-(2-Iminopiperidino)pentyl]-3-oxo-3,4-dihydro-2-
quinoxalinylbenzenecarboximidamide;

3-3-Oxo-4-[5-(4-oxopiperidino)pentyl]-3,4-dihydro-2-
quinoxalinylbenzenecarboximidamide;

3-[4-(5-2-[(Dimethylamino)methyl]piperidinopentyl)-3-
oxo-3,4-dihydro-2-quinoxalinyl]
benzenecarboximidamide;

3-(4-5-[4-(Dimethylamino)piperidino]pentyl-3-oxo-3,4-
dihydro-2-quinoxalinyl)benzenecarboximidamide;

1-5-[3-3-[Amino(imino)methyl]phenyl-2-oxo-1(2H)-
quinoxalinyl]pentyl-4-piperidinesulfonic acid;

3-3-Oxo-4-[5-(2-phenylpiperidino)pentyl]-3,4-dihydro-2-
quinoxalinylbenzenecarboximidamide;

3-4-[5-(2,5-Dimethyl-1-pyrrolidinyl)pentyl]-3-oxo-3,4-
dihydro-2-quinoxalinylbenzenecarboximidamide;

3-3-Oxo-4-[5-(1-pyrrolidinyl)pentyl]-3,4-dihydro-2-
quinoxalinylbenzenecarboximidamide;

1-5-[3-3-[Amino(imino)methyl]phenyl-2-oxo-1(2H)-
quinoxalinyl]pentyl-2-pyrrolidinecarboxylic acid;

N-(1-5-[3-3-[Amino(imino)methyl]phenyl-2-oxo-1(2H)-
quinoxalinyl]pentyltetrahydro-1H-pyrrol-3-yl)-N-
methylacetamide;

3-4-[5-(3-Amino-1-pyrrolidinyl)pentyl]-3-oxo-3,4-dihydro-
2-quinoxalinylbenzenecarboximidamide;

3-(4-5-[2,5-bis(Methoxymethyl)-1-pyrrolidinyl]pentyl-3-
oxo-3,4-dihydro-2-quinoxalinyl)
benzenecarboximidamide;

3-(4-5-[2-(Hydroxymethyl)-1-pyrrolidinyl]pentyl-3-oxo-3,
4-dihydro-2-quinoxalinyl)benzenecarboximidamide;

3-(4-5-[2-(Hydroxymethyl)-5-methyl-1-pyrrolidinyl]
pentyl-3-oxo-3,4-dihydro-2-quinoxalinyl)
benzenecarboximidamide;

3-4-[5-(Diisopropylamino)pentyl]-3-oxo-3,4-dihydro-2-
quinoxalinylbenzenecarboximidamide;

3-4-[5-(Diethylamino)pentyl]-3-oxo-3,4-dihydro-2-
quinoxalinylbenzenecarboximidamide;

3-4-[5-(Methylamino)pentyl]-3-oxo-3,4-dihydro-2-
quinoxalinylbenzenecarboximidamide;

3-4-[5-(1-Methyl-1H-imidazol-2-yl)pentyl]-3-oxo-3,4-
dihydro-2-quinoxalinylbenzenecarboximidamide;

3-4-[5-(2,5-Dimethyl-1H-imidazol-1-yl)pentyl]-3-oxo-3,4-
dihydro-2-quinoxalinylbenzenecarboximidamide;

3-[4-(5-Morpholinopentyl)-3-oxo-3,4-dihydro-2-
quinoxalinyl]benzenecarboximidamide;

3-4-[5-(3,5-Dimethylmorpholino)pentyl]-3-oxo-3,4-
dihydro-2-quinoxalinylbenzenecarboximidamide;

3-[3-Oxo-4-(5-piperazinopentyl)-3,4-dihydro-2-
quinoxalinyl]benzenecarboximidamide;

3-4-[5-(2,6-Dimethylpiperazino)pentyl]-3-oxo-3,4-dihydro-
2-quinoxalinylbenzenecarboximidamide;

3-3-Oxo-4-[5-(1H-pyrazol-1-yl)pentyl]-3,4-dihydro-2-
quinoxalinylbenzenecarboximidamide;

3-[3-Oxo-4-(5-tetrahydro-1H-pyrazol-1-ylpentyl)-3,4-
dihydro-2-quinoxalinyl]benzenecarboximidamide;

3-4-[5-(2,5-Dimethyltetrahydro-1H-pyrazol-1-yl)pentyl]-3-
oxo-3,4-dihydro-2-
quinoxalinylbenzenecarboximidamide;

3-(6-Chloro-4-5-[(2R,6S)-2,6-dimethyltetrahydro-1(2H)-
pyridinyl]pentyl-3-oxo-3,4-dihydro-2-quinoxalinyl)
benzenecarboximidamide;

3-(4-5-[(2R,6S)-2,6-Dimethyltetrahydro-1(2H)-pyridinyl]
pentyl-6-fluoro-3-oxo-3,4-dihydro-2-quinoxalinyl)
benzenecarboximidamide;

3-(4-5-[(2R,6S)-2,6-Dimethyltetrahydro-1(2H)-pyridinyl]
pentyl-3-oxo-6-sulfanyl-3,4-dihydro-2-quinoxalinyl)
benzenecarboximidamide;

3-[4-5-[(2R,6S)-2,6-Dimethyltetrahydro-1(2H)-pyridinyl]
pentyl-6-(methylsulfanyl)-3-oxo-3,4-dihydro-2-
quinoxalinyl]benzenecarboximidamide;

3-(4-5-[(2R,6S)-2,6-Dimethyltetrahydro-1(2H)-pyridinyl]
pentyl-3-oxo-6-(trifluoromethyl)-3,4-dihydro-2-
quinoxalinyl)benzenecarboximidamide;

3-(4-5-[(2R,6S)-2,6-Dimethyltetrahydro-1(2H)-pyridinyl]
pentyl-6-methyl-3-oxo-3,4-dihydro-2-quinoxalinyl)
benzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinecarboxylic acid;
Methyl 2-3-[amino(imino)methyl]phenyl-4-5-[(2R,6S)-2,6-dimethyltetrahydro-1(2H)-pyridinyl]pentyl-3-oxo-3,4-dihydro-6-quinoxalinecarboxylate;
3-(6-Cyano-4-5-[(2R,6S)-2,6-dimethyltetrahydro-1(2H)-pyridinyl]pentyl-3-oxo-3,4-dihydro-2-quinoxalinyl)benzenecarboximidamide;
2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinecarboximidamide;
2-3-[Amino(imino)methyl]phenyl-4-5-[(2R,6S)-2,6-dimethyltetrahydro-1(2H)-pyridinyl]pentyl-N-hydroxy-3-oxo-3,4-dihydro-6-quinoxalinecarboximidamide;
3-4-5-[(2R,6S)-2,6-Dimethyltetrahydro-1(2H)-pyridinyl]pentyl-6-[hydrazino(imino)methyl]-3-oxo-3,4-dihydro-2-quinoxalinylbenzenecarboximidamide;
2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinecarboxamide;
3-[4-5-[(2R,6S)-2,6-Dimethyltetrahydro-1(2H)-pyridinyl]pentyl-6-(hydroxymethyl)-3-oxo-3,4-dihydro-2-quinoxalinyl]benzenecarboximidamide;
3-(6-(Aminomethyl)-4-5-[(2R,6S)-2,6-dimethyltetrahydro-1(2H)-pyridinyl]pentyl-3-oxo-3,4-dihydro-2-quinoxalinyl)benzenecarboximidamide;
3-(4-5-[(2R,6S)-2,6-Dimethyltetrahydro-1(2H)-pyridinyl]pentyl-6-nitro-3-oxo-3,4-dihydro-2-quinoxalinyl)benzenecarboximidamide;
3-(4-5-[(2R,6S)-2,6-Dimethyltetrahydro-1(2H)-pyridinyl]pentyl-6-hydroxy-3-oxo-3,4-dihydro-2-quinoxalinyl)benzenecarboximidamide;
3-(4-5-[(2R,6S)-2,6-Dimethyltetrahydro-1(2H)-pyridinyl]pentyl-6-methoxy-3-oxo-3,4-dihydro-2-quinoxalinyl)benzenecarboximidamide;
3-(6-(Benzyloxy)-4-5-[(2R,6S)-2,6-dimethyltetrahydro-1(2H)-pyridinyl]pentyl-3-oxo-3,4-dihydro-2-quinoxalinyl)benzenecarboximidamide;
2-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)oxy]acetic acid;
3-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)oxy]propanoic acid;
4-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)oxy]butanoic acid;
2-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)amino]acetic acid;
3-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)amino]propanoic acid;
4-[(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)amino]butanoic acid;
3-[4-5-[(2R,6S)-2,6-Dimethyltetrahydro-1(2H)-pyridinyl]pentyl-6-(2-hydroxyethoxy)-3-oxo-3,4-dihydro-2-quinoxalinyl]benzenecarboximidamide;
3-[4-5-[(2R,6S)-2,6-Dimethyltetrahydro-1(2H)-pyridinyl]pentyl-3-oxo-6-(1H-1,2,3,4-tetraazol-5-ylmethoxy)-3,4-dihydro-2-quinoxalinyl]benzenecarboximidamide;
3-(6-Amino-4-5-[(2R,6S)-2,6-dimethyltetrahydro-1(2H)-pyridinyl]pentyl-3-oxo-3,4-dihydro-2-quinoxalinyl)benzenecarboximidamide;
3-(6-(Butylamino)-4-5-[(2R,6S)-2,6-dimethyltetrahydro-1(2H)-pyridinyl]pentyl-3-oxo-3,4-dihydro-2-quinoxalinyl)benzenecarboximidamide;
3-(6-(Dimethylamino)-4-5-[(2R,6S)-2,6-dimethyltetrahydro-1(2H)-pyridinyl]pentyl-3-oxo-3,4-dihydro-2-quinoxalinyl)benzenecarboximidamide;
3-(6-Anilino-4-5-[(2R,6S)-2,6-dimethyltetrahydro-1(2H)-pyridinyl]pentyl-3-oxo-3,4-dihydro-2-quinoxalinyl)benzenecarboximidamide;
3-(6-(Benzylamino)-4-5-[(2R,6S)-2,6-dimethyltetrahydro-1(2H)-pyridinyl]pentyl-3-oxo-3,4-dihydro-2-quinoxalinyl)benzenecarboximidamide;
N-(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)acetamide;
N-(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)cyclohexanecarboxamide;
N-(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)-2-cyclohexylacetamide;
N-(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)benzenecarboxamnide;
N-(2-3-[Amino(imino)methyl]phenyl-4-5-[(2R,6S)-2,6-dimethyltetrahydro-1(2H)-pyridinyl]pentyl-3-oxo-3,4-dihydro-6-quinoxalinyl)-2-phenylacetamide;
3-4-5-[(2R,6S)-2,6-Dimethyltetrahydro-1(2H)-pyridinyl]pentyl-6-[(methylsulfonyl)amino]-3-oxo-3,4-dihydro-2-quinoxalinylbenzenecarboximidamide;
3-(6-[(Cyclohexylsulfonyl)amino]-4-5-[(2R,6S)-2,6-dimethyltetrahydro-1(2H)-pyridinyl]pentyl-3-oxo-3,4-dihydro-2-quinoxalinyl)benzenecarboximidamide;
3-(6-[(Cyclohexylmethyl)sulfonyl]amino-4-5-[(2R,6S)-2,6-dimethyltetrahydro-1(2H)-pyridinyl]pentyl-3-oxo-3,4-dihydro-2-quinoxalinyl)benzenecarboximidamide;
7-Chloro-1-(3-dimethylamino-propyl)-3-phenyl-1H-quinoxalin-2-one;
7-Chloro-1-(3-dimethylamino-propyl)-3-phenyl-1H-quinoxalin-2-one;
3-(4-Chloro-phenyl)-7-methoxy-1-(4-methoxy-phenyl)-1H-quinoxalin-2-one;
2(1H)-Quinoxalinone, 7-methoxy-1,3-bis(p-methoxyphenyl);
3-(3-Chloro-phenyl)-7-methoxy-1-(4-methoxy-phenyl)-1H-quinoxalin-2-one;
3-(4-Fluoro-phenyl)-7-methoxy-1-(4-methoxy-phenyl)-1H-quinoxalin-2-one;
3-(3,4-Dichloro-phenyl)-7-methoxy-1-(4-methoxy-phenyl)-1H-quinoxalin-2-one;
1-(2-Diethylamino-ethyl)-4-oxy-3-phenyl-1H-quinoxalin-2-one;
1-(2-Diethylamino-ethyl)-4-oxy-3-phenyl-1H-quinoxalin-2-one;
3-(2-Chloro-phenyl)-7-methoxy-1-(4-methoxy-phenyl)-1H-quinoxalin-2-one;
3-(4-Bromo-phenyl)-7-methoxy-1-(4-methoxy-phenyl)-1H-quinoxalin-2-one;
2(1H)-Quinoxalinone, 7-methoxy-1-(p-methoxyphenyl)-3-phenyl;
7-Methoxy-1-(4-methoxy-phenyl)-3-(4-trifluoromethyl-phenyl)-1H-quinoxalin-2-one;
2(1H)-Quinoxalinone, 1-methyl-3-phenyl-, 4-oxide;
7-Methoxy-1-(4-methoxy-phenyl)-3-(3-trifluoromethyl-phenyl)-1H-quinoxalin-2-one;
7-Methoxy-1-(4-methoxy-phenyl)-3-p-tolyl-1H-quinoxalin-2-one;
3-(2-Fluoro-phenyl)-7-methoxy-1-(4-methoxy-phenyl)-1H-quinoxalin-2-one;
1-(3-Diethylamino-propyl)-3-phenyl-1H-quinoxalin-2-one;

7-Hydroxy-1-(4-hydroxy-phenyl)-3-phenyl-1H-quinoxalin-2-one;

3-(4-Chloro-phenyl)-1-phenyl-1H-quinoxalin-2-one;

2(1H)-Quinoxalinone, 1,3-diphenyl;

1-[5-(2,6-Dimethyl-piperidin-1-yl)-pentyl]-3-phenyl-1H-quinoxalin-2-one;

3-{4-[5-(2,6-Dimethyl-piperidin-1-yl)-pentyl]-1-methyl-3-oxo-1,2,3,4-tetrahydro-quinoxalin-2-yl}-N-hydroxy-benzamidine;

3-{4-[5-(2,6-Dimethyl-piperidin-1-yl)-pentyl]-3-oxo-3,4-dihydro-quinoxalin-2-yl}-N-hydroxy-benzamide;

3-(3-Amino-1H-indazol-5-yl)-1-[5-(2,6-dimethyl-piperidin-1-yl)-pentyl]-1H-quinoxalin-2-one;

2(1H/)-Quinoxalinone, 1-[2-(diethylamino)ethyl]-3-[[4-(methoxy)phenyl]methyl];

3-4-5-[(2R,6S)-2,6-Dimethyltetrahydro-1(2H7)-pyridinyl]pentyl-3-oxo-6-[(phenylsulfonyl)amino]-3,4-dihydro-2-quinoxalinylbenzenecarboximidamide; and 3-(6-[(Benzylsulfonyl)amino]-4-5-[(2R,6S)-2,6-dimethyltetrahydro-1(2H)-pyridinyl]pentyl-3-oxo-3,4-dihydro-2-quinoxalinyl)benzenecarboximidamide.

DETAILED DESCRIPTION OF THE INVENTION

The term "alkyl" means a straight, branched, saturated or unsaturated carbon chain having from 1 to 20 carbon atoms. Typical alkyl groups include methyl, isobutyl, pentyl, 2-methyl-pentyl, pent-1,4-dienyl, but-1-enyl and the like.

The term "cycloalkyl" means a saturated or unsaturated carbon chain which forms a ring having from 3 to 20 carbon atoms. Typical examples include cyclopropyl, cyclohexyl and the like.

The term "cycloalkylalkyl" means a cycloalkyl group attached to an alkyl group wherein "cycloalkyl" and "alkyl" are as defined above and includes, for example, cyclopropylmethyl, cyclopentylethyl and the like.

The term "heteroalkyl" means a straight, branched, saturated or unsaturated carbon chain having from 1 to 20 carbon atoms wherein one or more carbon atoms is replaced by a heteroatom selected from oxygen, nitrogen, sulfur, sulphoxide, or sulphone. Typical "heteroalkyl" groups include methoxymethyl, 3-thiomethylpropyl, and 2-thiomethoxyethoxymethyl and the like.

The term "aryl" represents an unsaturated carbocyclic ring(s) of 6 to 16 carbon atoms which is optionally substituted with, OH, O(alkyl), SH, S(alkyl), amine, halogen, acid, ester, amide, alkyl ketone, aldehyde, nitrile, fluoroalkyl, nitro, sulphone, sulfoxide, or (C$_{1-6}$)alkyl. Typical rings include phenyl, naphthyl, phenanthryl, and anthracenyl. Preferred aryl rings are phenyl, substituted phenyl, and naphthyl.

The term "arylalkyl" means an aromatic radical attached to an alkyl radical wherein "aryl" and "alkyl" are as defined above and includes, for example, benzyl and naphthylmethyl.

The term "heterocycle" means a saturated or unsaturated mono- or polycyclic (i.e., bicyclic) ring incorporating one or more (i.e., 1–4) heteroatoms selected from N, O, and S. It is understood that a heterocycle is optionally substituted with OH, O(alkyl), SH, S(alkyl), amine, halogen, acid, ester, amide, alkyl ketone, aldehyde, nitrile, fluoroalkyl, nitro, sulphone, sulfoxide, or C$_{1-6}$ alkyl. Examples of suitable monocyclic heterocycles include, but are not limited to, substituted or unsubstituted thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyrimidinyl, piperidinyl, pyrrolidinyl, piperazinyl, azetidinyl, aziridinyl, morpholinyl, thietanyl, oyetanyl. Preferred monoydicheterocycles include, but are not limited to, 2- or 3- thienyl; 2- or 3-furanyl; 1-, 2-, or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1,3-, or 5-triazolyl; 1-, 2-, or 3-tetrazolyl; 2, 3-, or 4-pyridinyl; 2-pyrazinyl; 2-, 4-, or 5-pyrimidinyl; 1-, 2-, 3-, or 4-piperidinyl; 1-, 2-, or 3-pyrrolidinyl; 1- or 2-piperazinyl; 1-, 2-, or 3-azetidinyl; 1- or 2-aziridinyl; 2-, 3-, or 4-morpholinyl; 2- or 3-thietanyl; 2- or 3-oxetanyl. Examples of suitable bicyclic heterocycles include, but are not limited to, indolizinyl, isoindolyl, benzothienyl, benzoxazolyl, benzimidazolyl, quinolinyl, isoquinolinyl, and preferably 1-, 2-, 3-, 4-, 5-, 6-, or 7-indolyl; 1-, 2-, 3-, 5-, 6-, 7-, or 8-indolizinyl; 1-, 2-, 3-, 4-, 5-, 6-, or 7-isoindolyl; 2-, 3-, 4-, 5-, 6-, or 7-benzothienyl; 2-, 4-, 5-, 6-, or 7-benzoxazolyl; 1-, 2-, 4-, 5-, 6-, or 7-benzimidazolyl; 2-, 3-, 4-, 5-, 6-, 7-, or 8-quinolinyl; 1-, 3-, 4-, 5-, 6-, 7-, or 8-isoquinolinyl.

The term "heteroatom" as used herein represents oxygen, nitrogen, or sulfur (O, N, or S) as well as sulfoxyl or sulfonyl (SO or SO$_2$) unless otherwise indicated. It is understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl.

The term "amine" refers to a group such as NH$_2$, NHalkyl, NH(cycloalkyl), NH(cycloalkylalkyl), NH(aryl), NH(arylalkyl), NH(heteroaryl), NH(heteroarylalkyl), N(alkyl)(alkyl), N(alkyl)(cycloalkyl), N(alkyl)(cycloalkylalkyl), N(alkyl)(aryl), N(alkyl)(arylalkyl), N(alkyl)(heteroaryl), N(alkyl)(heteroarylalkyl), N(cycloalkyl)(cycloalkyl), N(cycloalkyl)(cycloalkylalkyl), N(cycloalkyl)(aryl), N(cycloalkyl)(arylalkyl), N(cycloalkyl)(heteroaryl), N(cycloalkyl)(heteroarylalkyl), N(cycloalkylalkyl)(cycloalkylalkyl), N(cycloalkylalkyl)(aryl), N(cycloalkylalkyl)(arylalkyl), N(cycloalkylalkyl)(heteroaryl), N(cycloalkylalkyl)(heteroarylalkyl), N(aryl)(cycloalkylalkyl), N(aryl)(aryl), N(aryl)(arylalkyl), N(aryl)(heteroaryl), N(aryl)(heteroarylalkyl), N(arylalkyl)(arylalkyl), N(arylalkyl)(heteroaryl), N(arylalkyl)(heteroarylalkyl), N(heteroaryl)(heteroaryl), N(heteroaryl)(heteroarylalkyl), N(heteroarylalkyl)(heteroarylalkyl).

The term "acid" refers to C(=O)OH.

The term "ketone" refers to C(=O)alkyl, C(=O)cycloalkyl, C(=O)cycloalkylalkyl, C(=O)aryl, C(=O)arylalkyl, C(=O)heteroaryl, C(=O)heteroarylalkyl.

The term "ester" refers to a group such as C(=O)Oalkyl, C(=O)Ocycloalkyl, C(=O)Ocycloalkylalkyl, C(=O)Oaryl, C(=O)Oarylalkyl, C(=O)Oheteroaryl, C(=O)Oheteroarylalkyl.

The term "amide" refers to a group such as C(=O)NH$_2$, C(=O)NHalkyl, C(=O)NH(cycloalkyl), C(=O)NH(cycloalkylalkyl), C(=O)NH(aryl), C(=O)NH(arylalkyl), C(=O)NH(heteroaryl), C(=O)NH(heteroarylalkyl), C(=O)N(alkyl)(alkyl), C(=O)N(alkyl)(cycloalkyl), C(=O)N(alkyl)(cycloalkylalkyl), C(=O)N(alkyl)(aryl), C(=O)N(alkyl)(arylalkyl), C(=O)N(alkyl)(heteroaryl), C(=O)N(alkyl)(heteroarylalkyl), C(=O)N(cycloalkyl)(cycloalkyl), C(=O)N(cycloalkyl)(cycloalkylalkyl), C(=O)N(cycloalkyl)(aryl), C(=O)N(cycloalkyl)(arylalkyl), C(=O)N(cycloalkyl)(heteroaryl), C(=O)N (cycloalkyl)(heteroarylalkyl), C(=O)N(cycloalkylalkyl)(cycloalkylalkyl), C(=O)N(cycloalkylalkyl)(aryl), C(=O)N(cycloalkylalkyl)(arylalkyl), C(=O)N(cycloalkylalkyl)(heteroaryl), C(=O)N(cycloalkylalkyl)(heteroarylalkyl), C(=O)N(aryl)(cycloalkylalkyl), C(=O)N(aryl)(aryl), C(=O)N(aryl)(arylalkyl), C(=O)N(aryl)(heteroaryl), C(=O)N(aryl)(heteroarylalkyl), C(=O)N(arylalkyl)(arylalkyl), C(=O)N(arylalkyl)(heteroaryl), C(=O)N(arylalkyl)(heteroarylalkyl), C(=O)N(heteroaryl)(heteroaryl), C(=O)N(heteroaryl)(heteroarylalkyl), C(=O)N(heteroarylalkyl)(heteroarylalkyl).

The term "urea" refers to a group such as NHC(=O)N(alkyl)(alkyl), NHC(=O)N(alkyl)(cycloalkyl), NHC(=O)N(alkyl)(cycloalkylalkyl), NHC(=O)N(alkyl)(aryl), NHC(=O)N(alkyl)(arylalkyl), NHC(=O)N(alkyl)(heteroaryl), NHC(=O)N(alkyl)(heteroarylalkyl), NHC(=O)N(cycloalkyl)(cycloalkyl), NHC(=O)N(cycloalkyl)(cycloalkylalkyl), NHC(=O)N(cycloalkyl)(aryl), NHC(=O)N(cycloalkyl)(arylalkyl), NHC(=O)N(cycloalkyl)(heteroaryl), NHC(=O)N(cycloalkyl)(heteroarylalkyl), NHC(=O)N(cycloalkylalkyl)(cycloalkylalkyl), NHC(=O)N(cycloalkylalkyl)(aryl), NHC(=O)N(cycloalkylalkyl)(arylalkyl), NHC(=O)N(cycloalkylalkyl)(heteroaryl), NHC(=O)N(cycloalkylalkyl)(heteroarylalkyl), NHC(=O)N(aryl)(cycloalkylalkyl), NHC(=O)N(aryl)(aryl), NHC(=O)N(aryl)(arylalkyl), NHC(=O)N(aryl)(heteroaryl), NHC(=O)N(aryl)(heteroarylalkyl), NHC(=O)N(arylalkyl)(arylalkyl), NHC(=O)N(arylalkyl)(heteroaryl), NHC(=O)N(arylalkyl)(heteroarylalkyl), NHC(=O)N(heteroaryl)(heteroaryl), NHC(=O)N(heteroaryl)(heteroarylalkyl), NHC(=O)N(heteroarylalkyl)(heteroarylalkyl).

The term "halogen" refers to chlorine, fluorine, bromine, and iodine.

The wedge or hash is only one representation of a stereochemical descriptor. All stereoisomers, including enantiomers and diastereomers, are included within Formulas I to V and are provided by this invention. When specific isomers are drawn, they are the preferred isomers.

In some situations, compounds may exist as tautomers. All tautomers are included within Formulas I to V and are provided by this invention.

When compounds are administered, some metabolism may occur. All metabolites are included within Formulas I to V and are provided by this invention.

When a bond to a substituent is shown to cross the bond connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring.

When a bond is represented by a line such as " --- ," this is meant to represent that the bond may be absent or present provided that the resultant compound is stable and of satisfactory valency.

Compounds of the present invention are capable of forming acid addition salts (see, for example, Berge S. M. et al., "Pharmaceutical Salts," *Journal of Pharmaceutical Science*, 1977:1–10) with inorganic acids such as, for example, hydrochloric acid, sulfuric acid and the like, as well as salts derived from organic acids such as, for example, aliphatic mono- and dicarboxylic acids or aliphatic and aromatic sulphonic acids. The acid addition salts are prepared by contacting the free base form with a sufficient amount of the desired acid to produce the salt. The free base form may be regenerated by contacting the salt form with a base. While the free base more may differ from the salt form in terms of physical properties, such as solubility, the salts are equivalent to their respective free bases for the purposes of the present invention.

Certain compounds of the present invention can exist in unsolvated form as well as solvated form including hydrated form. In general, the solvated form including hydrated form is equivalent to unsolvated form and is intended to be encompassed within the scope of the present invention.

"Prodrugs" are intended to include any covalently bonded carrier which releases the active parent drug according to Formulas I to V in vivo. Examples of prodrugs include acetates, formates, benzoate derivatives of alcohols and amines present in compounds of Formulas I to V. They also include derivatives of the amidine or guanine functionality and would include C(=NR$_3$)NH$_2$ where R$_3$ is selected from OH, NH$_2$, C$_{1-4}$ alkoxy, C$_{6-10}$ aryloxy, C$_{1-10}$ alkoxycarbonyl, C$_{6-10}$ aryloxycarbonyl. Preferred derivatives include examples wherein R$_3$ is OH, NH$_2$, methoxy, and ethoxycarbonyl.

The following table provides a list of abbreviations and definitions thereof used in the present invention.

| Abbreviation | Description |
| --- | --- |
| AMC | aminomethylcoumarin |
| aPTT | activated partial thromboplastin time |
| BOC | tertiary-butyloxycarbonyl |
| BOP-reagent | benzotriazol-1-yloxy-tris(dimethylamino) phosphonium hexafluorophosphate |
| Bz | benzoate |
| CDCl$_3$ | deuterochloroform |
| DMF | dimethyl formamide |
| DMSO | dimethylsulfoxide |
| $^1$H-NMR | proton nuclear magnetic resonance |
| HCl | hydrogen chloride |
| HF | hydrogen fluoride |
| HMPA | hexamethylphosphoramide |
| HPLC | high pressure liquid chromatography |
| MOT | mean occlusion time |
| MS (APCI) | mass spectrometry (atmospheric pressure CI) |
| MS (CI) | mass spectrometry (chemical ionization) |
| MS (ES) | mass spectrometry (electro spray) |
| NaOH | sodium hydroxide |
| nBuLi | n-butyl lithium |
| NH$_4$Cl | ammonium chloride |
| Pd/C | palladium on carbon |
| PtO$_2$ | platinum oxide |
| r.t. or RT | room temperature |
| TFA | trifluoroacetic acid |
| THF | tetrahydrofuran |
| TT | thrombin time |
| VAZO-52 | 2,2'-azobis-2-methylvaleronitrile |

Also provided by this invention is a method for preventing and treating acute, subacute, and chronic thrombotic disorder in a mammal comprising administering to such mammal an effective amount of a compound of Formulas I to V. The compounds are useful as anticoagulants for the treatment and prophylaxis of disorders such as venous and arterial thrombosis, pulmonary embolism, and ischemic events such as myocardial infarction or cerebral infarction. These compounds also have therapeutic utility for the prevention and treatment of complications of indwelling vascular access ports and arteriovenous shunts and coagulpathies associated with cardiopulmonary bypass or other extra corporeal systems. These compounds are useful for preventing or treating unstable angina, intermittent claudication refractory angina, disseminated intravascular coagulation, and ocular buildup of fibrin. Since thrombin and serine proteases have also been demonstrated to activate a number of different cell types, these compounds are useful for the treatment or prophylaxis of septic shock and other inflammatory responses such as acute or chronic atherosclerosis. The compounds also have utility in treating neoplasia/metastasis and neurodegenerative diseases such as Alzheimer's and Parkinson's disease. In a preferred method, the thrombotic disorder is selected from venous thrombosis, arterial thrombosis, pulmonary embolism, myocardial infarction, cerebral infarction, angina, cancer, and diabetes. A further embodiment of this invention is a pharmaceutical formulation comprising a compound of Formulas I to V administered with a diluent, excipient, or carrier thereof.

Preparation of Compounds of the Invention

The compounds of Formulas I to V can be prepared by any of various methods known to those skilled in the art of organic chemistry. The following general schemes represent preferred routes to provide the compounds of this disclosure. The reactions are typically performed in solvents appropriate to the reagents and substrates employed. It is understood that functionality present in the molecule must be compatible with the reagents and reaction conditions proposed. Not all compounds of Formulas I to V falling into a given class may be compatible with some of the reaction conditions described. Such restrictions are readily apparent to those skilled in the art of organic synthesis, and alternative methods must then be used.

Compounds of the present invention may be prepared by a number of synthetic sequences. One such preferred route is outlined in Scheme 1.

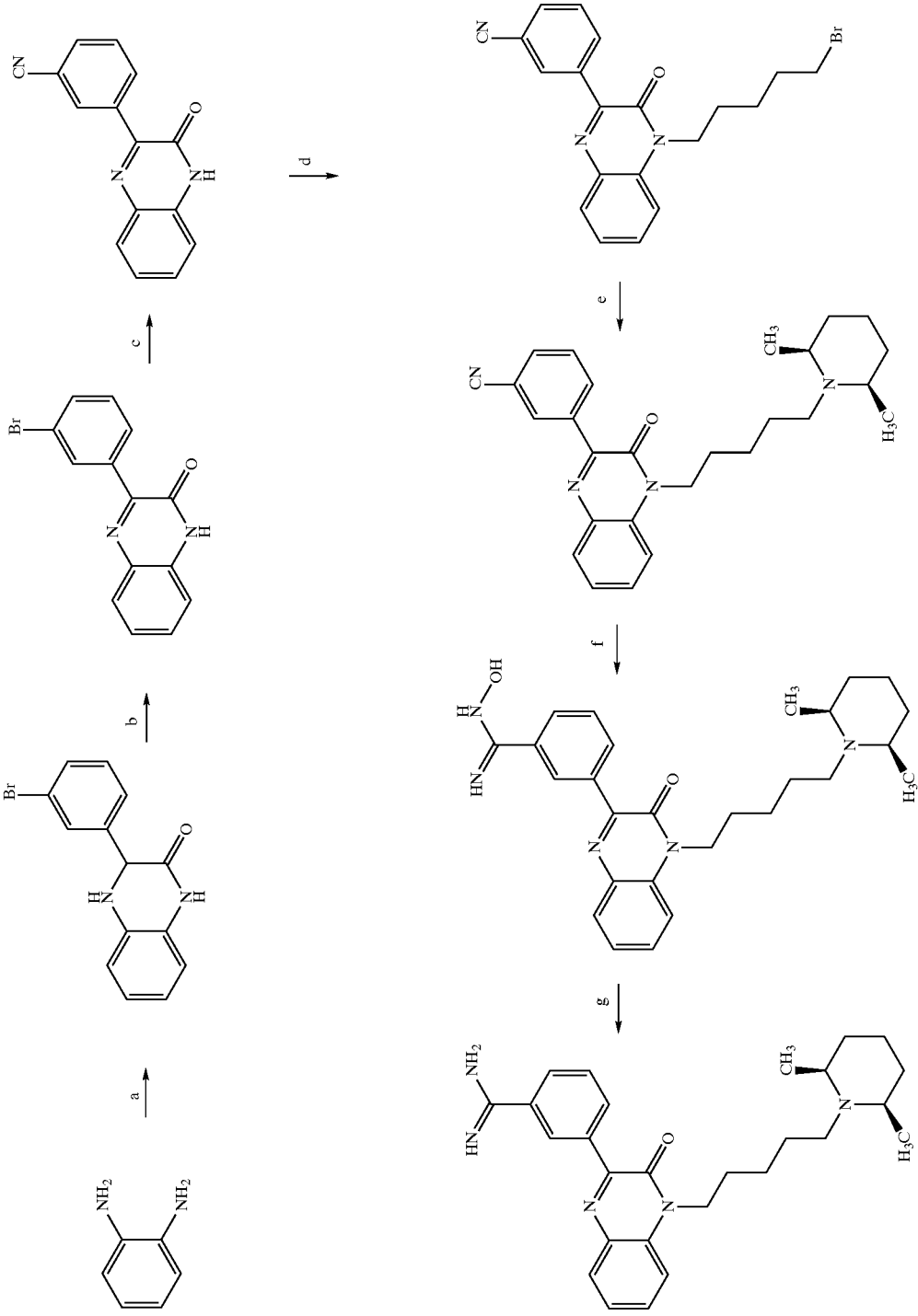

Step a:
Ortho-phenylenediamine is treated with a suitably substituted bromoacetic acid derivative, such as 2-bromo-2-(3-bromophenyl)acetic acid, in basic medium, such as aqueous sodium hydroxide, which upon warming to 60° C. and then maintaining at this temperature for 30 minutes, affords the product 3-(3-bromophenyl)-1,2,3,4-tetrahydro-2-quinoxalinone as a precipitate.

Step b:
Simply treating the tetrahydroisoquinoline with an oxidant, such as dichloro dicyanobenzoquinone (DDQ), or lead tetraacetate, and warming in toluene, affords the product 3-(3-bromophenyl)-1,2-dihydro-2-quinoxalinone, which may be purified by, for example, recrystallisation.

Step c:
The aryl bromide is converted to the corresponding nitrile by, for example, treatment with copper cyanide in a solvent such as DMF. Typically, the reaction mixture is warmed to 160° C. and maintained at this temperature for several hours, typically 12, to afford the required product. Alternatively, the bromide, or iodide, or triflate is converted to the nitrile by treatment with a transition metal, such as palladium tetrakis triphenylphosphine and zinc cyanide. The mixture is then warmed in a solvent such as DMF, typically to a temperature of 80° C. for several hours or until the reaction is judged complete, by for example TLC.

Step d:
Alkylation is typically achieved by treatment with an appropriate electrophile and by the addition of a base in a dipolar aprotic solvent. Typical conditions include, for example, use of a bis-electrophilic substrate such as 1,5-dibromopentane in a dipolar aprotic solvent such as DMF or DMSO and addition of a base, such as sodium hydride. Alternatively, alkylation can be achieved by the addition of a phase transfer reagent such as an alkylammonium salt, such as benzyltriethylammonium chloride, and employing a base such as sodium ethoxide. Reaction rates are typically improved by the application of heat, and hence, reactions are run at from 0° C. to 70° C.

Step e:
Treatment with an amine, such as cis-2,6-dimethylpiperidine at an elevated temperature such as 50° C. affords the expected N-alkylated piperidine. The amine may be used as solvent, or alternatively, the amine may be added in stoichiometric proportions and the reaction mixture refluxed in a solvent such as ethanol, acetonitrile, or toluene. The product, as the appropriate acid addition salt, is then neutralized by the addition of base such as aqueous potassium hydroxide, and isolated by extraction with an organic solvent such as ethylacetate.

Step f:
Conversion of the nitrile to the hydroxyamidine is achieved by allowing the nitrile to react with hydroxylamine in methanol at room temperature. Typically, hydroxylamine hydrochloride is added to the nitrile containing substrate at room temperature, and the reaction is initiated by the addition of base such as potassium carbonate or diisopropylethylamine.

Step g:
The amidoxime may be reduced directly, but is typically activated by the addition of acetic anhydride of trifluoroacetic anhydride to afford the O-acylated, or O-trifluoroacetyl, intermediate, which may be isolated or alternatively used directly in the subsequent reduction step. Steps g and h may be combined; i.e., the reduction with Pd/C is performed in acetic anhydride/acetic acid, or trifluoroacetic anhydride/trifluoroacetic acid.

Step h:
The substrate is dissolved in methanol, or acetic acid, or trifluoroacetic acid, and treated with a transition metal catalyst such as Palladium dispersed on carbon and is then hydrogenated briefly, typically for 1 to 12 hours, at 50 psi, in a solvent such as methanol or ethanol. The product is then isolated, typically by crystallization or via chromatography such as reverse phase HPLC.

An alternative procedure for the preparation of compounds of Formula I involves that shown in Scheme 2, similar to the procedure of M. C. Alamanni Farmaco, *Ed. Sci.*, 1981;36(5):359 and Ahmad A. R., *Tetrahedron* 1995;51 (47): 12899–12910.

Scheme 2

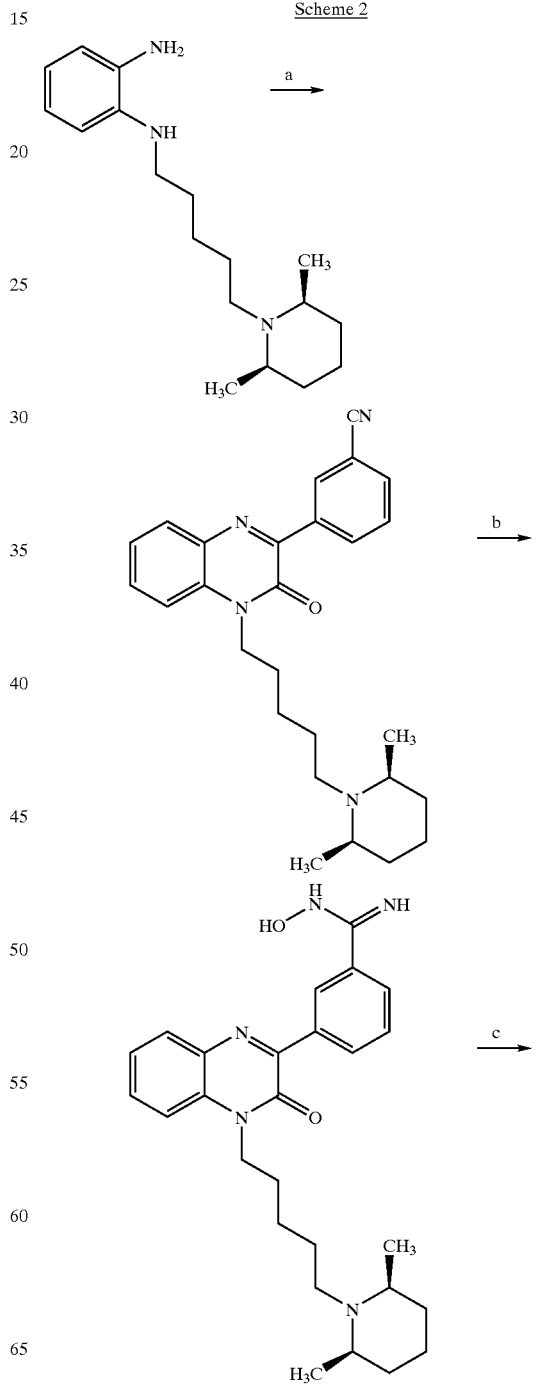

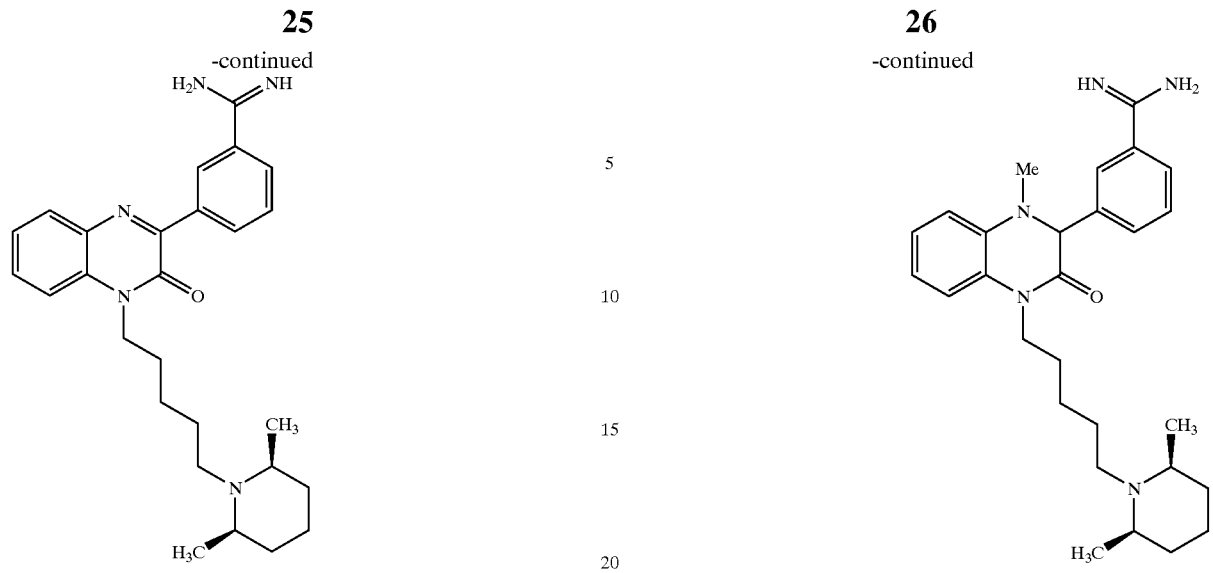

Step a:

Treatment of [N-5-(2,6-dimethylpiperidyl)pentyl]-ortho-phenylenediamine with methyl 2-(3-cyanophenyl)-2-oxoacetate in, for example, ethanol affords the expected quinoxalinone.

Steps b and c:

Similar to the procedure discussed in Scheme 1 the nitrile is converted to the corresponding amidine.

An alternative procedure to prepare compounds of Formula I is outlined in Scheme 3.

Scheme 3

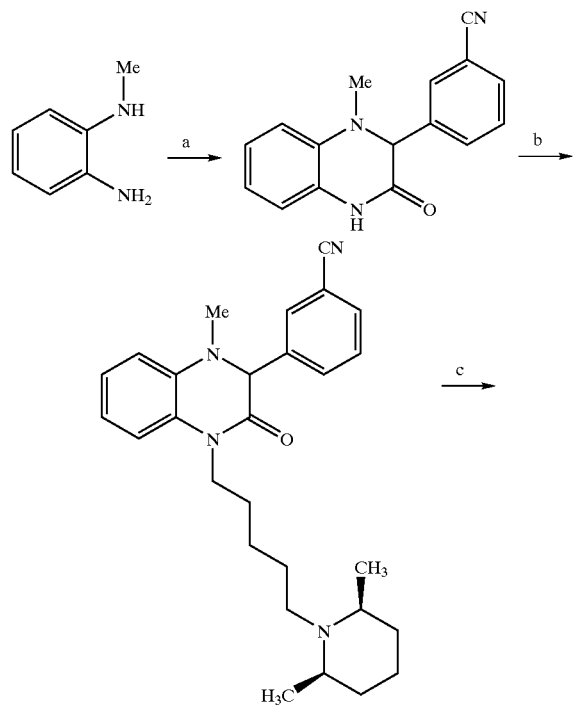

Step a:

Treatment of (2-aminophenyl)methylamine with 2-bromo-2-(3-cyanophenyl)acetic acid, by way of specific example, affords the quinoxalinone. Typically, the reaction is performed in the presence of aqueous base with the application of external heating such that the reaction mixture is maintained at a temperature of about 60° C. for several hours, typically two. In favorable situations, the product precipitates directly from the reaction mixture. The product may also be isolated by extraction of the reaction mixture with ethylacetate, and the required regioisomer is isolated by crystallization or chromatography on silica gel. The predominant regioisomer is that drawn.

Step b:

The intermediate is then alkylated with, for example, 1-(5-bromopentyl)-2,6-dimethylpiperidine by treatment of the quinoxalinone with sodium hydride in a solvent such as DMF at from 0° C. to 50° C. Accordingly, the N versus O regioisomers are separated by chromatography. Alternatively, 1,5-dibromopentane may be used in excess and the required N-alkyl-bromide isolated by chromatography. A separate step is then required to convert the bromide to, for example, 2,6-dimethylpiperidine. This transformation is achieved by heating the bromide in neat 2,6-dimethylpiperidine, typically around 80° C.

Step c:

The final step involves conversion of the nitrile to the amidine, and hence may be accomplished by the procedure outlined above, by way of an amidoxime intermediate, or by treatment of the nitrile with anhydrous hydrogen chloride in an alcoholic solvent, such as methanol to afford the intermediate imino ether. This intermediate is then treated with a source of ammonia, such as ammonium acetate to afford the required amidine.

The substituted alpha-bromo phenylacetates used in these reactions are prepared by a number of standard procedures, such as, for example, that shown in Scheme 4.

Scheme 4

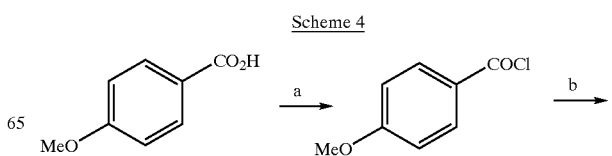

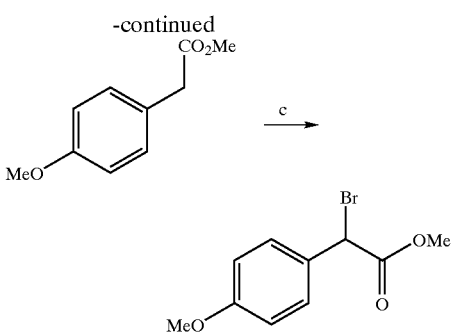

Step a:
Acetic acid derivatives are prepared by conversion of the substituted benzoic acid to the corresponding acid chloride with, for example, oxalyl chloride and catalytic DMF and is then treated with ethereal diazomethane.

Step b:
Rearrangement with silver oxide in an alcoholic solvent, such as methanol, affords the homologated acetic acid methyl ester.

Step c:
Functionalization of the alpha position is then achieved by refluxing a solution of the ester in carbon tetrachloride with N-bromosuccinimide in the presence of a radical initiator such as AIBN.

An alternative procedure involves treatment of acetic acid derivatives with bromine in the presence of phosphorus tribromide will afford the alphabromo phenyl acetate in a manner typical of the Hell-Volhard-Zelinskii reaction.

Alternatively, the intermediate alpha bromo ester may be prepared by the procedure shown in Scheme 5.

Scheme 5

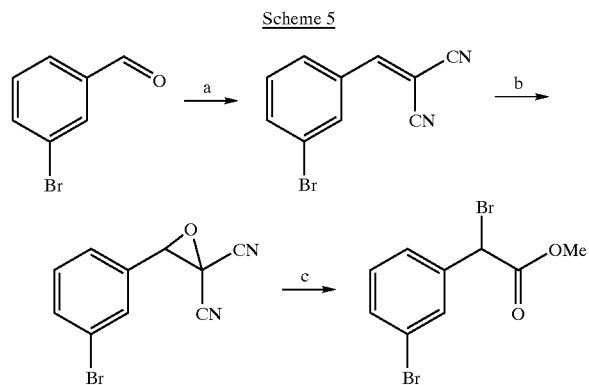

Step a:
In this situation the aldehyde, such as 3-bromobenzaldehyde as a representative example, is reacted with malonitrile in the presence of catalytic piperidine in a solvent such as dioxane to afford the 2-[(3-bromophenyl)methylene]malononitrile.

Step b:
Epoxide formation proceeds readily with commercial bleach at a pH of 5 to 6.

Step c:
Treatment with hydrobromic acid in methanol then affords the required methyl 2-bromo-2-(3-bromophenyl) acetate; alternatively, use of hydrobromic acid in the absence of an alcoholic solvent then affords the corresponding acid derivative.

Alternative procedures for the conversion of nitrites to amidines are also available. Treatment of the nitrile with hydrogen chloride in an alcoholic solvent affords the corresponding iminoether hydrochloride. These intermediates are then treated with source of ammonia, for example, ammonia in methanol, or ammonium chloride, or ammonium acetate, and the mixture is stirred and warmed, if necessary, to afford the amidine. The nitriles, in turn, are available by, for example, a palladium catalyzed cross-coupling reaction with $Zn(CN)_2$.

Scheme 6 demonstrates yet another method that may be employed to prepare compounds of this invention and is similar to that reported by Holley et al. *J. Amer. Chem. Soc.,* 1952, 74, 5445–5448 and Kirk et al. *J. Org. Chem.,* 1969, 34, 395.

Scheme 6

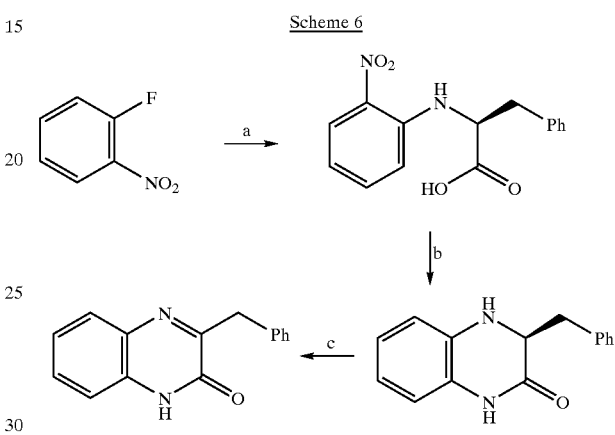

Step a:
In this situation a natural or unnatural amino acid, such as L-phenylalanine, or 2-amino-2-[2-(benzyloxy)-5-cyanophenyl]acetic acid is combined with an ortho fluoronitrobenzene in a solvent such as ethanol with additional base such as sodium bicarbonate and the mixture heated. Advantageously the nitro benzene substrate is substituted para to the fluoro substituent, with for example a carbomethoxy substituent such that the addition reaction with an amino acid (or peptide derivative) may proceed at a lower temperature.

Step b:
Reduction of the nitro substituent to afford an intermediate aniline may proceed by way of hydrogenation over a transition metal catalyst such as palladium on carbon in a solvent such as water and base (sodium bicarbonate for example). Rapid intramolecular cyclization then proceeds, upon neutralization, to afford the required intermediate 3,4-dihydro-quinoxalinone.

Step c:
Treatment of the dihydroquinoxalinone with an oxidant such as DDQ affords the intermediate quinoxalinone, which may then be elaborated as described in scheme 1 to afford, for example, the desired factor Xa inhibitors such as 3-(4-5-[(2R,6S)-2,6-dimethyltetrahydro-1(2H)-pyridinyl]pentyl-3-oxo-3,4-dihydro-2-quinoxalinyl)-4-hydroxybenzenecarboximidamide.

Compounds of the present invention are further characterized by their ability to inhibit the catalytic activity of factor Xa, which is demonstrated in the assay as follows. Compounds of the present invention may be prepared for assay by dissolving them in buffer to give solutions ranging in concentrations from 1 to 100 $\mu$M. In an assay to determine the inhibitory dissociation constant, $K_i$, for a given compound, a chromogenic or fluorogenic substrate of factor Xa would be added to a solution containing a test compound and factor Xa; the resulting catalytic activity of the enzyme is spectrophotometrically determined. This assay is well-known to those skilled in the art and is commonly used to determine antithrombotic activity.

The compounds of the present invention may be used as anti-coagulants in vitro or ex vivo as in the case of contact activation with foreign thrombogenic surfaces, such as is found in tubing used in extracorporeal shunts. The compounds of the invention may also be used to coat the surface of such thrombogenic conduits. To this end, the compounds of the invention can be prepared as lyophilized powders, redissolved in isotonic saline or similar diluent, and added in an amount sufficient to maintain blood in an anticoagulated state.

The therapeutic agents of the present invention may be administered alone or in combination with pharmaceutically acceptable carriers. The proportion of each carrier is determined by the solubility and chemical nature of the compound, the route of administration, and standard pharmaceutical practice. For example, the compounds may be injected parenterally; this being intramuscularly, intravenously, or subcutaneously. For parenteral administration, the compound may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may also be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and/or flavoring agents. Typical formulations will contain from about 5 to 95 percent by weight of an invention compound.

The amount of invention compound to be utilized to prevent and treat thrombotic disorders is that amount which is effective to prevent or treat the condition without causing unacceptable side effects. Such effective amounts will be from about 0.01 mg/kg to about 500 mg/Kg, preferably from about 1 mg/kg to about 100 mg/kg. Physicians will determine the precise dosage of the present therapeutic agents which will be most suitable. Dosages may vary with the mode of administration and the particular compound chosen. In addition, the dosage may vary with the particular patient under treatment.

When the composition is administered orally, a larger quantity of the active agent will typically be required to produce the same effect as caused with a smaller quantity given parenterally.

To further assist in understanding the present invention, the following non-limiting examples of such factor Xa inhibitory compounds are provided. The following examples, of course, should not be construed as specifically limiting the present invention, variations presently known or later developed, which would be within the purview of one skilled in the art and considered to fall within the scope of the present invention as described herein. The preferred compounds as of the present invention are synthesized using conventional preparative steps and recovery methods known to those skilled in the art of organic and bio-organic synthesis, while providing a new and unique combination for the overall synthesis of each compound. Preferred synthetic routes for intermediates involved in the synthesis, as well as the resulting anti-thrombotic compounds of the present invention, follow.

EXAMPLES

In general, evaporation of reaction mixtures was carried out by rotary evaporation in vacuo at room temperature 18° C. to 25° C. or at elevated temperatures up to 50° C. Chromatography, preferably by medium pressure liquid chromatography, were generally performed on Merck Kieselgel. Reverse phase purification via high pressure liquid chromatography (HPLC), for particular polar compounds, was performed on C-18 reverse phase silica gel employing a gradient elution of water and acetonitrile containing 0.1% trifluoroacetic acid. The final products displayed nuclear magnetic resonance (NMR) spectra and mass spectra consistent with their assigned structure. Intermediates were not typically fully characterized and their purity was routinely assessed by HPLC or thin layer chromatography.

Example 1

3-[3-(Amidino)phenyl]-1-{5-[(2R,6S)-2,6-dimethylhexahydro-1-pyridinyl]pentyl}-1,2-dihydro-2-quinoxalinone Step (a): Preparation of 3-(3-Bromophenyl)-1,2,3,4-tetrahydro-2-quinoxalinone

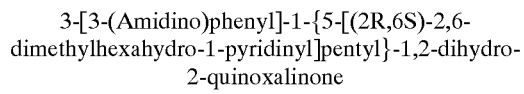

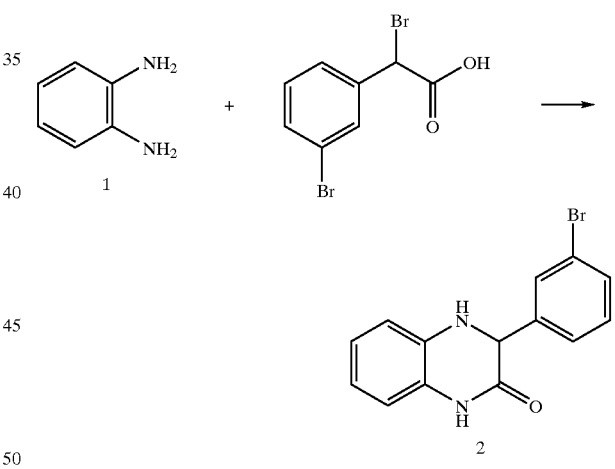

2-Bromo-2-(3-bromophenyl)acetic acid (4.95 g, 16.9 mmol) was added to an aqueous (40 mL) solution of sodium hydroxide (0.67 g, 16.8 mmol). Ortho-phenylenediamine (1.82 g, 16.9 mmol) was added and the mixture transferred to an oil bath at 60° C. After 30 minutes, the solid that had separated was collected, washed with water, and then dried under vacuum. Recrystallization from ethanol and water afforded the required product (2).

(APCI MS) 303 and 305. Anal. $C_{14}H_{11}N_2O_1Br_1$: Found: C, 55.27; H, 3.45; N, 8.94. Required: C, 55.47; H, 3.66; N, 9.24. $^1$H NMR (DMSO, 400 MHz): δ 10.47 (1H, s), 7.51 (1H, s), 7.46 (1H, d, J=7.7 Hz), 7.28 (2H, m), 6.8–6.6 (3H, m), 6.60 (1H, m), 4.96 (1H, s).

Step (b): Preparation of 3-(3-Bromophenyl)-1,2-dihydro-2-quinoxalinone

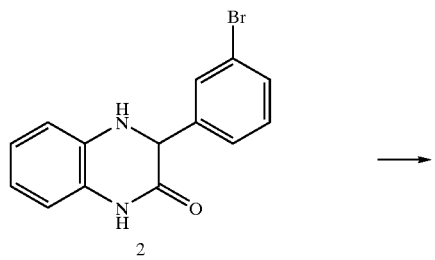

To (2) (1.73 g, 5.7 mmol) in toluene (50 mL) was added 2,3-dichloro-5,6-dicyano-1,4-benzoquinone {DDQ} (1.30 g, 5.7 mmol). The mixture was refluxed for 3 hours, cooled, and then filtered. This solid was triturated with ethanol to afford analytically pure product (3) (1.14 g, 66%).

(APCI MS) 301 and 303. Anal. $C_{14}H_9N_2O_1Br_1$: Found: C, 55.96; H, 2.88; N, 9.15. Required: C, 55.84; H, 3.01; N, 9.30. $^1$H NMR (DMSO, 300 MHz): δ 12.62 (1H, s), 8.46 (1H, m), 8.27 (1H, d, J=7.8 Hz), 7.80 (1H, d, J=8.0 Hz), 7.66 (1H, m), 7.44 (1H, m), 7.40 (1H, m), 7.29 (2H, m).

Step (c): Preparation of 3-(3-Cyanophenyl)-1,2-dihydro-2-quinoxalinone

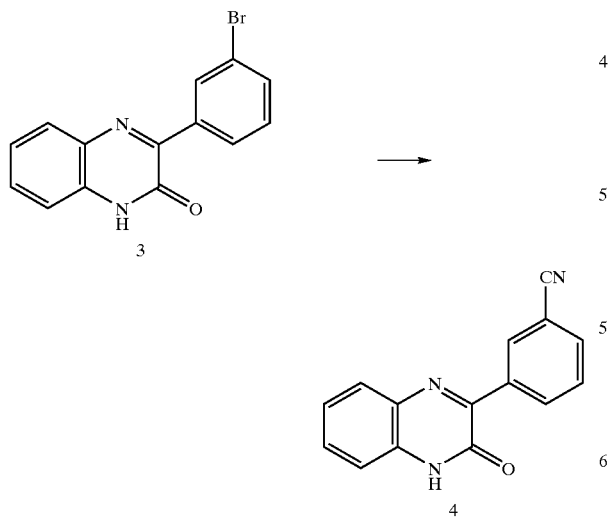

To the quinoxalinone (3) (0.581 g, 1.93 mmol) in DMF (4 mL) was added copper (1) cyanide (0.343 g, 3.82 mmol) and the mixture heated under nitrogen in a sealed tube at 160° C. for 12 hours. The mixture was cooled, diluted with ethyl acetate (50 mL), and washed with aqueous ammonium hydroxide (2×10 mL). After washing with brine, the organic phase was dried over magnesium sulfate and then evaporated in vacuo to afford (4) (0.316 g, 66%).

$^1$H NMR (DMSO, 300 MHz): δ 8.76 (1H, brs), 8.27 (1H, dt, J=8.4 Hz), 7.95 (1H, d, J=7.9 Hz), 7.82 (1H, d, J=7.0 Hz), 7.69 (1H, t, J=8.1 Hz), 7.51 (1H, t, J=1.3 Hz), 7.24 (2H, m).

Step (d): Preparation of 1-[5-Bromopentyl]-3-(3-cyanophenyl)-1,2-dihydro-2-quinoxalinone

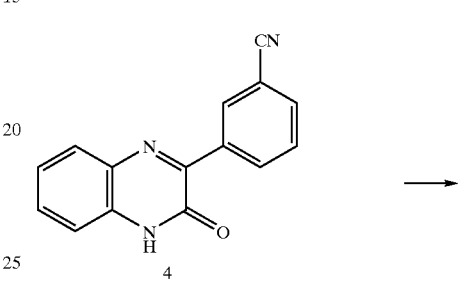

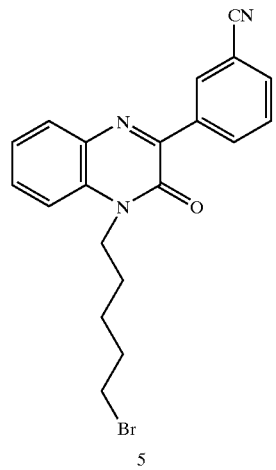

To (4) (0.39 g, 1.58 mmol) in DMF (3 mL) was added sodium hydride (60% in oil, 0.070 g, 1.75 mmol) and then 1,5-dibromopentane (0.65 mL, 3 equiv.). The mixture was stirred at 0° C. for 6 hours, diluted with water (20 mL), and then extracted into ethylacetate (100 mL). After washing with brine and drying over magnesium sulfate, the product (5) (0.287 g, 46%) was isolated by chromatography on silica gel, eluant 80% hexane in ethylacetate (a less polar compound: 2-[(5-bromopentyl)oxy]-3-(3-cyanophenyl)quinoxaline was also isolated (0.179 g, 29%)).

$^1$H NMR (DMSO, 300 MHz): δ 8.64 (1H, m), 8.53 (1H, dt, J=8.0 Hz), 7.99 (1H, dt, J=7.8 Hz), 7.93 (1H, dt, J=7.8 Hz), 7.68 (3H, m), 7.40 (1H, m), 4.30 (2H, t, J=7.3 Hz), 3.54 (2H, t, J=6.8 Hz), 1.87 (2H, m), 1.71 (2H, m), 1.52 (2H, m).

Step (e): Preparation of 3-[3-(Cyano)phenyl]-1-{5-[(2R,6S)-2,6-dimethylhexahydro-1-pyridinyl]pentyl}-1,2-dihydro-2-quinoxalinone

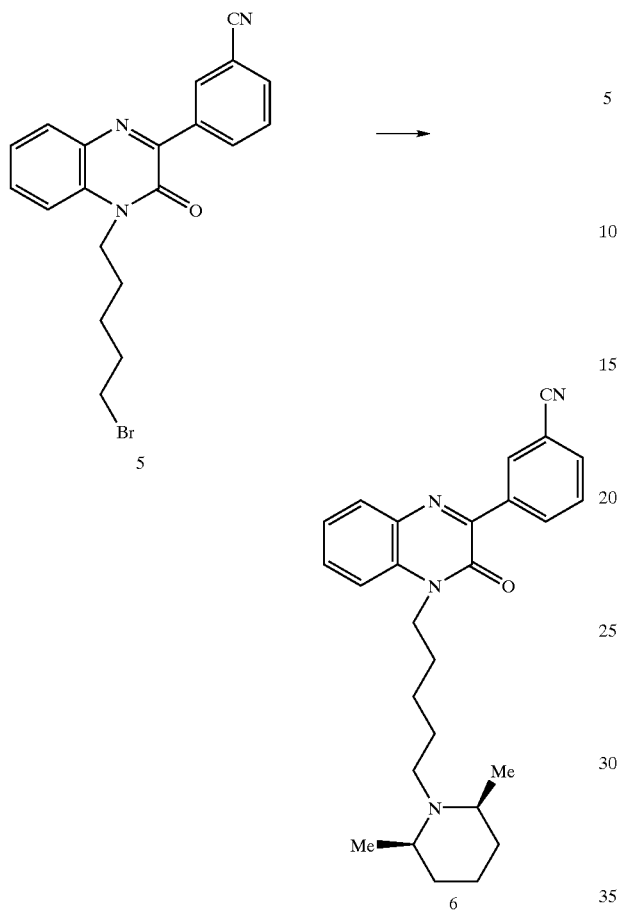

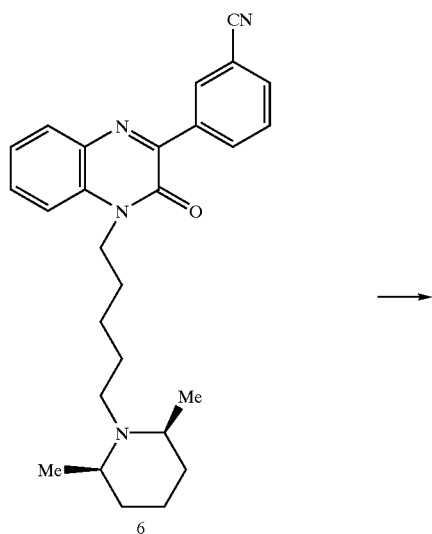

To (5) (0.285 g, 0.72 mmol) was added cis-2,6-dimethylpiperidine (5 mL), and then the mixture was heated at 50° C. for 16 hours. The mixture was evaporated in vacuo to afford the required product (6) sufficiently pure for subsequent reactions.

(APCI MS) 428.

Step (f): Preparation of 3-[3-(Amidino)phenyl]-1-{5-[(2R,6s)-2,6-dimethylhexahydro-1-pyridinyl]pentyl}-1,2-dihydro-2-quinoxalinone To (6) (0.10 g, 0.24 mmol) in ethanol (5 mL) was added hydroxylamine hydrochloride (0.164 g, 2.36 mmol) and then diisopropylethylamine (0.4 mL, 2.30 mmol). The mixture was stirred at room temperature for 16 hours and then extracted into ethylacetate (50 mL) from ammonium hydroxide (5 mL). After a brine wash, the intermediate amidoxime was isolated by evaporation in vacuo. This process affords 0.08 g of intermediate, HPLC: RT=9.27 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM). (MS APCI) 461. The amidoxime (0.08 g) was dissolved in acetic acid (1 mL) and treated with acetic anhydride (5 mL). After 1 hour, the mixture was evaporated in vacuo to afford the acetylated intermediate 0.09 g, HPLC: RT=11.79 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Trifluoroacetic acid (5 mL) was added to the acetylated intermediate (0.09 g) and then palladium on carbon (20%) (0.04 g) was added. The mixture was evacuated, and then a hydrogen balloon was attached. After 16 hours, the mixture was filtered, evaporated, and purified by reverse phase HPLC (Vydac 218TP1022 C-18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nM) and was lyophilized to give 23 mg of product (7) as an oil/solid.

¹H NMR (DMSO, 300 MHz): δ 10.4 (1H, bs), 9.36 (2H, d, J=11.1 Hz), 9.10 (1H, brs), 8.57 (1H, d, J=7.7 HZ), 8.19 (1H, bs), 8.12 (1H, dt, J=7.9 Hz), 7.91 (1H, t, J=7.3 Hz), 7.8–7.6 (4H, m), 3.99 (2H, t, J=7.0 Hz), 3.40 (2H, brd), 3.02 (2H, m), 2.80 (2H, m), 1.98–1.4 (16H, m). (APCI MS) 446. HPLC: RT=8.49 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Example 2

3-(4-5-[(2R,6S)-2,6-dimethyltetrahydro-1(2H)-pyridinyl]pentyl-3-oxo-3,4-dihydro-2-quinoxalinyl)-4-hydroxybenzenecarboximidamide Step (a): Preparation of 2-(benzyloxy)-5-bromobenzenecarbaldehyde

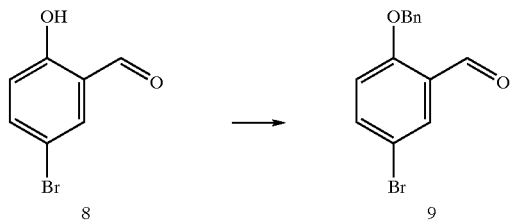

5-Bromosalicylaldehyde (8) (100 g, 496 mmol) was dissolved in EtOH (300 mL) and a solution of KOH (27.8 g, 496 mmol) in H₂O (80 mL) was added. After stirring at ambient temperature for 30 min, benzyl bromide (71.2 mL, 596 mmol), which was previously passed through a plug of neutral alumina, was added. The resulting mixture was warmed to reflux for 18 h, at which time a colorless precipitate formed. After cooling to ambient temperature, H₂O (50 mL) was added and the title compound was filtered. After washing with H₂O the title compound (9) was recrystallized from EtOH to give 122 g (85%) of a colorless solid. ¹H NMR (400 MHz, CDCl₃) 10.46 (d, 1H); 7.90 (d, 1H); 7.56 (dd, 1H); 7.30 (m, 5H); 6.91 (d, 1H); 5.14 (s, 2H); MS 292(M⁺), 261(M-CHO) HPLC 20.45 min. (95% H₂O:5% CH₃CN)+0.1% TFA to (10% H₂O:90% CH₃CN)+0.1% TFA over 22 min on a Vyadec 218TP54 C₁₈ Column Step (b): Preparation of 2-[2-(benzyloxy)-5-bromophenyl]-2-hydroxyacetonitrile

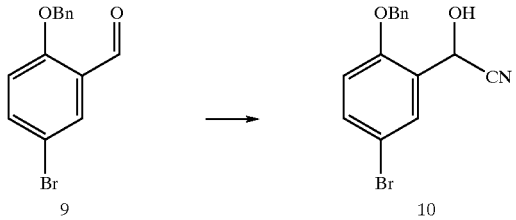

2-(Benzyloxy)-5-bromobenzenecarbaldehyde (9) (20 g, 69 mmol) was dissolved in MeOH (150 mL) and was then followed by the addition of potassium cyanide (20.1 g, 308 mmol). Acetic acid (6.3 mL, 109 mmol) was added dropwise over 20 min at ambient temperature. The resulting mixture was stirred at ambient temperature for 3 h. Acetic acid (2 mL) was added and the mixture was stirred for an additional 1 h. Additional acetic acid (30 mL) was added and the mixture was diluted with H₂O (60 mL). After concentration at reduced pressure, the aqueous residue was extracted with EtOAc (3×100 mL). The combined organics were washed with brine and dried over MgSO₄. Filtration and concentration left a pale yellow oil, which was without further purification. The title compound (10) could be isolated in pure form by gradient column chromatography (10 to 20% EtOAc in Hexanes). ¹H NMR (400 MHz, CDCl₃) 7.53 (d, 1H); 7.24 (m, 6H); 6.86 (d, 1H); 5.52 (d, 1H); 5.13 (s, 2H); 3.38 (d, 1H). MS 199, 201(M-Bn-CN). HPLC 20.40 min. (95% H₂O:5% CH₃CN)+0.1% TFA to (10% H₂O:90% CH₃CN)+0.1% TFA over 22 min on a Vyadec 218TP54 C₁₈ Column Step (c): Preparation of methyl 2-[2-(benzyloxy)-5-bromophenyl]-2-hydroxyacetate

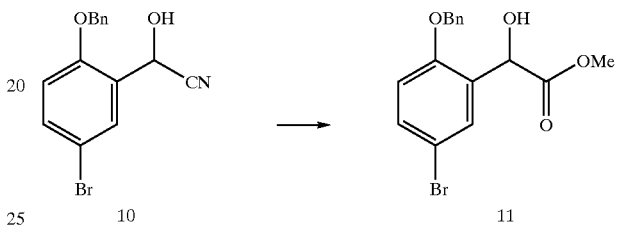

Crude 2-[2-(benzyloxy)-5-bromophenyl]-2-hydroxyacetonitrile (10), from above, was dissolved in anhydrous dioxane (25 mL), ether (25 mL) and MeOH (6 mL). After cooling the mixture to 0° C., it was saturated with HCl gas and warmed to ambient temperature. A precipitate formed and the mixture was stirred for 1.5 h. [If the mixture became too viscous to stir, anhydrous ether was added]. The reaction mixture was diluted with ether (200 mL) and filtered. The colorless solid was washed with ether and used as is.

The solid was suspended in H₂O (60 mL) and dioxane (60 mL) and stirred vigorously for approximately 4 h. The reaction is complete when all solids have disappeared and an oily residue remains. The mixture was poured into H₂O (150 mL) and extracted with EtOAc (3×100 mL). The combined organics were washed with brine and dried over MgSO₄. Filtration and concentration yielded the crude title compound, which was used without purification. The title compound (11) could be isolated in pure form by column chromatography (15% EtOAc in Hexanes). ¹H NMR (400 MHz, CDCl₃) 7.4 (m, 7H), 6.82 (m, 1H), 5.32 (d, 1H), 5.90 (ABq, 2H), 3.70 (s, 3H), 3.63 (d, 2H). MS 352(M⁺). HPLC 17.5 min. (95% H₂O:5% CH₃CN)+0.1% TFA to (10% H₂O:90% CH₃CN)+0.1% TFA over 22 min on a Vyadec 218TP54 C₁₈ Column Step (d): Preparation of methyl 2-[2-(benzyloxy)-5-bromophenyl]-2-oxoacetate

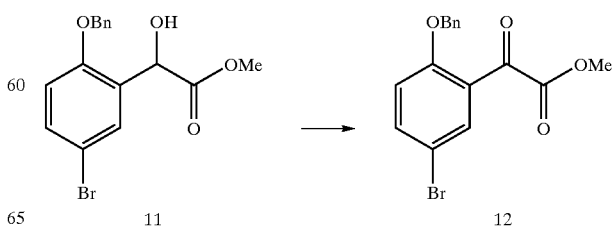

Dimethyl sulfoxide (12.4 mL, 164 mmol) was added slowly to a solution of oxalyl chloride (7.2 mL, 82.4 mmol) in $CH_2Cl_2$ (100 mL) at −78° C. After addition the mixture was stirred at −78° C. for 15 min. A solution of methyl 2-[2-(benzyloxy)-5-bromophenyl]-2-hydroxyacetate (11) (68.6 mmol) in $CH_2Cl_2$ (60 mL) was added via a cannula. After stirring the mixture for 30 min at −78° C., triethylamine (47.8 mL, 343 mmol) was added and the mixture was allowed to warm to ambient temperature. After stirring the mixture for 1 h at ambient temperature, it was poured into $H_2O$ (200 mL). The layers were separated and the aqueous layer was washed with EtOAc (3×100 mL). The combined organics were washed with brine and dried over $MgSO_4$. After concentration, the title compound (12) was recrystallized from EtOAc/Hexanes to yield 13.5 g (60% from aldehyde) as a colorless solid. $^1H$ NMR (400 MHz, $CDCl_3$) 7.99 (d, 1H); 7.65 (dd, 1H); 7.40 (m, 5H); 6.95 (d, 1H); 5.06 (s, 2H); 3.34 (s, 3H). MS 256, 258($M^+$). HPLC 22.6 min. (95% $H_2O$:5% $CH_3CN$)+0.1% TFA to (10% $H_2O$:90% $CH_3CN$)+0.1% TFA over 22 min on a Vyadec 218TP54 $C_{18}$ Column Step (e): Preparation of 3-[2-(benzyloxy)-5-bromophenyl]-2(1H)-quinoxalinone

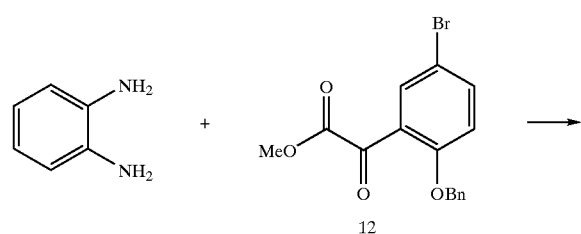

Methyl 2-[2-(benzyloxy)-5-bromophenyl]-2-oxoacetate (12) (7.0 g, 20 mmol) was dissolved in MeOH (60 mL) and 1,2-phenylenediamine was added (2.2 g, 20 mmol). The mixture was warmed to reflux overnight, at which time a percipitate was formed. The mixture was cooled to ambient temperature and $H_2O$ (10 mL) was added. The product was filtered and washed with a small amount of cold MeOH to yield 7.7 g (94%) of the title compound (13) as a colorless solid. $^1H$ NMR (400 MHz, DMSO) 12.54 (s, 1H); 7.73 (d, 1H); 7.65 (m, 2H); 7.23 (m, 8H); 7.10 (d, 1H); 5.08 (s, 2H). MS 407, 409($M^+$). HPLC 24.1 min. (95% $H_2O$ : 5% $CH_3CN$)+0.1% TFA to (10% $H_2O$ : 90% $CH_3CN$)+0.1% TFA over 22 min on a Vyadec 218TP54 $C_{18}$ Column Step (f): Preparation of 4-(benzyloxy)-3-(3-oxo-3,4-dihydro-2-quinoxalinyl)benzenecarbonitrile 3-[2-(Benzyloxy)-5-bromophenyl]-2(1H)-quinoxalinone (13) (20.4 g, 50 mmol) was dissolved in anhydrous DMF (200 mL) and then $Zn(CN)_2$ (3.52 g, 30 mmol) and $Pd(Ph_3P)_4$ (5.78 g, 5 mmol) were added. The resulting mixture was warmed to 100° C. for 5 h. The dark green solution was cooled to ambient temperature and stirred overnight. The title product (14) formed as a precipitate, which was separated by filtration and washed with ether. Yielded 12.3 g 69%. $^1H$ NMR (400 MHz, DMSO) 12.63 (s, 1H); 7.92 (dd, 1H); 7.87 (d, 1H); 7.79 (d, 1H); 7.58 (m, 1H); 7.2–7.4 (m, 8H); 5.24 (s, 2H). MS 354($M^+$). HPLC 16.4 min. (95% $H_2O$:5% $CH_3CN$)+0.1% TFA to (10% $H_2O$:90% $CH_3CN$)+0.1% TFA over 22 min on a Vyadec 218TP54 $C_{18}$ Column Step (g): Preparation of 4-(benzyloxy)-3-[4-(5-bromopentyl)-3-oxo-3,4-dihydro-2-quinoxalinyl]benzenecarbonitrile

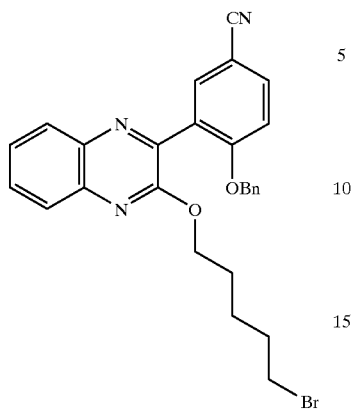

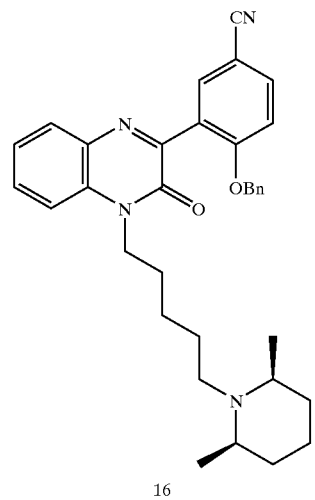

To a solution of 4-(benzyloxy)-3-(3-oxo-3,4-dihydro-2-quinoxalinyl)benzenecarbonitrile (14) (2 g, 5.7 mmol) in DMF (50 mL) was added Cs$_2$CO$_3$ (2.21 g, 6.8 mmol) at 0° C. The mixture was stirred for 30 min before the addition of 1,5-dibromopentane (4.62 mL, 40.0 mmol). The reaction mixture was stirred overnight, while slowly warming to ambient temperature, before being poured into H$_2$O (100 mL). The aqueous solution was extracted into EtOAc (3×100 mL). The combined organics were washed with brine and dried over MgSO$_4$. The title compound (15) (1.59 g, 53%, Rf=0.15 15% EtOAc in Hexanes) was isolated by gradient column chromatography (10 to 25% EtOAc in Hexanes) along with the O-alkylated analog (1.17 g, 41%, R$_f$=0.31 15% EtOAc in Hexanes). N-Alkylated: $^1$H NMR (400 MHz, CDCl$_3$) 7.90 (d, 2H); 7.88 (d, 1H); 7.70 (dd, 1H); 7.57 (t, 1H); 7.2–7.4 (m, 6H); 7.03 (d, 1H); 5.14 (s, 2H); 4.24 (t, 2H); 3.36 (t, 2H); 1.8–1.9 (m, 2H); 1.7–1.8 (m, 2H); 1.5–1.6 (m, 2H). MS 502, 504(M$^+$). HPLC 23.5 min. (95% H$_2$O:5% CH$_3$CN)+0.1% TFA to (10% H$_2$O:90% CH$_3$CN)+0.1% TFA over 22 min on a Vyadec 218TP54 C$_{18}$ Column Step (h): Preparation of 4-(benzyloxy)-3-(4-5-[(2R,6S)-2,6-dimethyltetrahydro-1(2H)-pyridinyl]pentyl-3-oxo-3,4-dihydro-2-quinoxalinyl)benzenecarbonitrile

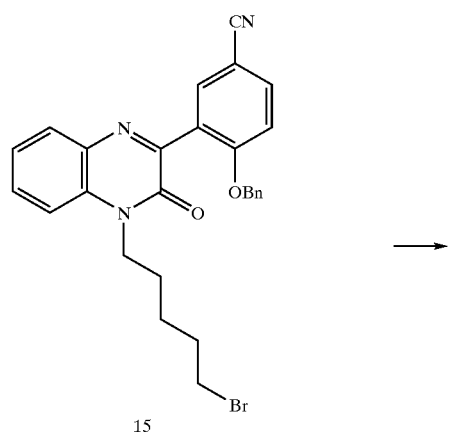

4-(Benzyloxy)-3-[4-(5-bromopentyl)-3-oxo-3,4-dihydro-2-quinoxalinyl]benzenecarbonitrile (15) (1.59 g, 3.17 mmol) was dissolved in anhydrous DMF (5 mL) and cis-2,6-dimethylpiperidine (15 mL) was added. The reaction mixture was warmed to 75° C. overnight. The reaction mixture was diluted with H$_2$O (50 mL) and extracted with EtOAc (2×20 mL). The combined organics were washed with brine, dried over MgSO$_4$ and concentrated to yield light yellow syrup, which was used without further purification (16). $^1$H NMR (400 MHz, DMSO) 7.95 (dd, 1H); 7.93 (d, 1H); 7.86 (d, 1H) 7.6–7.7 (m, 2H); 7.2–7.4 (m, 7H); 5.22 (s, 2H); 4.23 (t, 2H), 0.9–2.5 (m 22H). MS 535(M$^+$). HPLC 18.8 min. (95% H$_2$O:5% CH$_3$CN)+0.1% TFA to (10% H$_2$O:90% CH$_3$CN)+0.1 % TFA over 22 min on a Vyadec 218TP54 C$_{18}$ Column Step (i): Preparation of 3-(4-5-[(2R,6S)-2,6-dimethyltetrahydro-1(2H)-pyridinyl]pentyl-3-oxo-3,4-dihydro-2-quinoxalinyl)-4-hydroxybenzenecarboximidamide

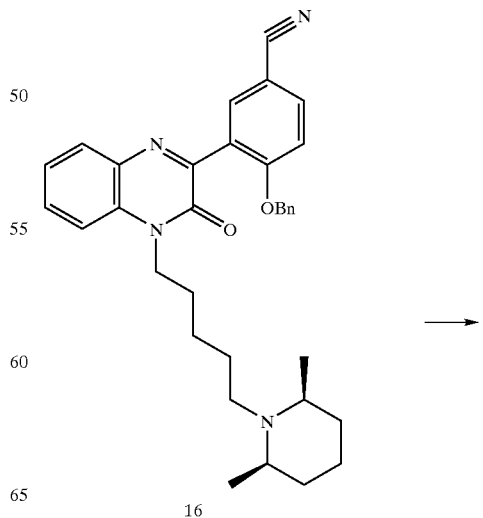

-continued

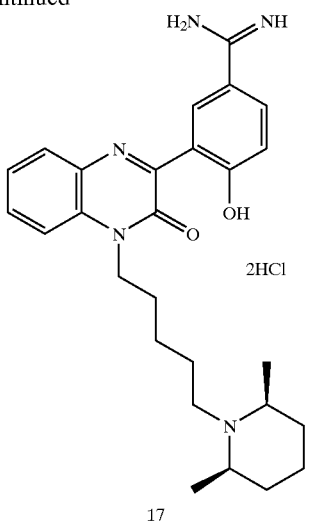

A solution of crude 4-(benzyloxy)-3-(4-5-[(2R,6S)-2,6-dimethyltetrahydro-1(2H)-pyridinyl]pentyl-3-oxo-3,4-dihydro-2-quinoxalinyl)benzenecarbonitrile (16) (assume 3.17 mmol), in anhydrous EtOH (20 mL), at 0° C. was saturated with $HCl_{(g)}$. The $HCl_{(g)}$ was bubbled through concentrated $H_2SO_4$ prior to the introduction to the reaction mixture. The reaction mixture stoppered and warmed to ambient temperature overnight, or until HPLC showed consumption of starting material and a new peak at 16.4 min. The mixture was concentrated in vauco and used without further purification.

The crude residue from above was dissolved in $NH_3$ (2M in EtOH, 20 mL) and stoppered. After stirring for 18 h at ambient temperature, HPLC showed complete consumption of starting materials and a new peak at 15.5 min.

The mixture was concentrated and the residue was submitted to the High pressure lab for hydrogenation (Pd/C, $H_2$, TFA, 24 h). HPLC showed a new peak at 14.3 min. The Mixture was concentrated and purified by prep-HPLC (100% $H_2O$+0.1% TFA to 20% $H_2O$:80% $CH_3CN$+0.1% TFA over 140 min) to yield PD 198961-0121b.

The lyophilized solid from above was dissolved in $H_2O$ (100 mL) and Amberlite 400(Cl) resin was added. After stirring for 3 h, the resin was filtered and the aqueous solution was lyophilized. The lyophilized solid was dissolved in MeOH (5 mL) and the product (17) was crystallized by the slow addition of a vast excess of EtOAc. Filtration yielded 198961-0002b as a yellow solid (630 mg, 30% from bromide). $^1$H NMR (400 MHz, DMSO) 9.14 (s, 1H); 9.00 (s, 1H); 8.34 (d, 1H); 7.91 (d, 1H); 7.81 (dd, 1H); 7.71 (m, 2H); 7.47 (m, 1H); 7.11 (d, 1H); 4.31 (m, 2H); 3.0–3.8 (m, 2H); 1.2–1.8 (m, 20H). MS 462(M$^+$). HPLC 14.3 min. (95% $H_2O$:5% $CH_3CN$)+0.1% TFA to (10% $H_2O$:90% $CH_3CN$)+0.1% TFA over 22 min on a Vyadec 218TP54 $C_{18}$ Column Intermediates 2-(3-Cyanophenyl)-3,4-dihydro-2H-1,4-benzoxazin-3-one Step (a): Preparation of 2-[(3-Cyanophenyl)methylene]malononitrile

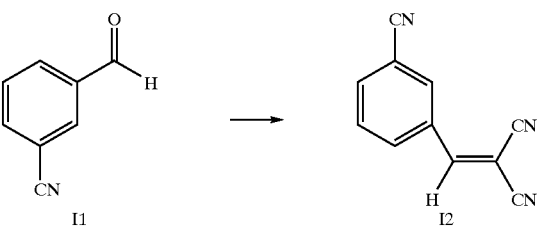

Into a mixture of 3-cyanobenaldehyde (I1) (24.8 g, 0.189 mol) and malononitrile (11.9 mL, 0.189 mol) in dioxane (120 mL) was added piperidine (1.5 mL) slowly. The solution was stirred at room temperature for 1 hour. The precipitate was filtered, washed with water, and dried in the high vacuum oven to give 7.11 g (21%) of product (12) as yellow solid. To the filtrate was added ethanol and water and 10.29 g (30%) of additional product crystallized as yellow solid.

$^1$H NMR (CDCl$_3$, 300 MHz): δ 8.17 (1H, m), 8.51 (1H, m), 7.87 (2H, m), 7.68 (1H, m).

Step (b): Preparation of 3-(3-Cyanophenyl)-2,2-oxiranedicarbonitrile

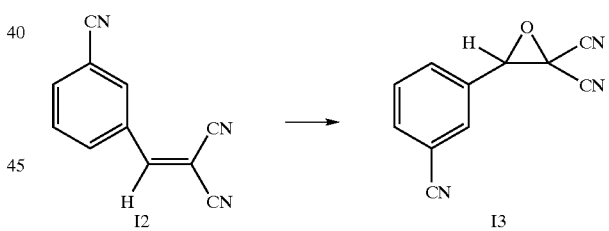

In a three-necked flask, intermediate (I2) (17.38 g, 97.0 mmol) was dissolved in acetonitrile (90 mL) and THF (113 mL) at room temperature with vigorous stirring. Sodium hypochlorite (183 mL) was added dropwise, while the pH of the solution was maintained between 4.5 and 6 throughout the addition by adding 2N sulfuric acid (20 mL). Once the addition was complete, stirring was continued for 20 minutes. Ethyl acetate was added, and the layers were separated. The aqueous layer was extracted with ethyl acetate (3×300 mL). The combined organic extracts were washed with brine (2×100 mL), dried with magnesium sulfate, filtered, and evaporated in vacuo. The residue was flushed through a pad of silica gel eluting with 50% ethyl acetate in hexane. The product (I3) was isolated 11.18 g (58%) as a tan solid.

$^1$H NMR (CDCl$_3$, 300 MHz): δ 7.83 (1H, m), 7.76 (1H, m), 7.67 (2H, m), 4.78 (1H, s).

Step (c): Preparation of 2-Bromo-2-(3-cyanophenyl)acetic acid

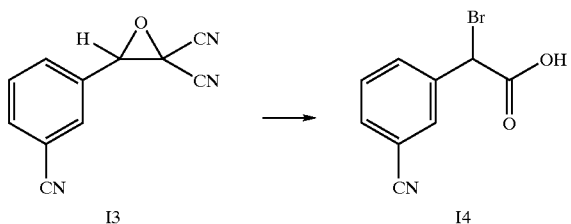

To the epoxide (I3) (5.12 g, 26.2 mmol) in THF (30 mL) was added 48% HBr (4.4 mL), and the solution was refluxed for 3 hours. The THF was removed in vacuo, and the residue was dissolved in ether (200 mL). The acid is extracted from ether with 1N NaOH (100 mL). The aqueous solution was then acidified with HCl, and the acid is extracted with ether (2×200 mL). The combined organic phases were dried over magnesium sulfate, filtered, evaporated in vacuo, and dried under high vacuum to give 4.32 g (69%) of (I4) as a brown oil.

$^1$H NMR (CDCl$_3$, 300 MHz): δ 7.83 (1H, m), 7.73 (1H, m), 7.55 (1H, m), 7.41 (1H, m), 5.26 (1H, s).

Step (d): Preparation of 2-Bromo-2-(3-cyanophenyl)acetyl chloride

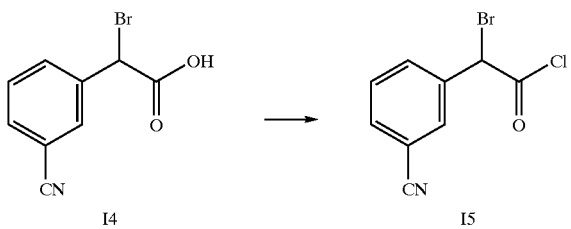

To the acid (I4) (1.01 g, 4.21 mmol) in dichloromethane (12 mL) were added oxalyl chloride (1 equiv.) and a catalytic amount of DMF (0.1 mL). Bubbling occurred and the resulting solution was stirred for 1 hour. The solvent was removed in vacuo to give (I5) in quantitative yield as a brown oil.

$^1$H NMR (CDCl$_3$, 300 MHz): δ 7.80–7.72 (3H, m), 7.592 (1H, m), 5.64 (1H, s).

Procedure for preparing Methyl 2-bromo-2-(3-bromophenyl)acetate

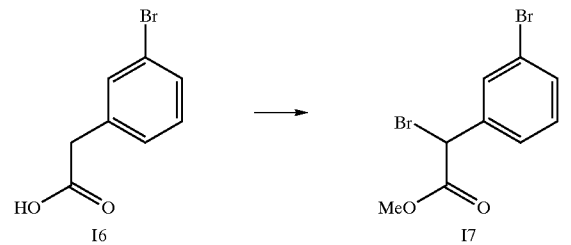

To 3-bromophenylacetic acid (16) (10 g, 47 mmol) under argon was added PBr$_3$ (11.2 mL, 118 mmol) and the suspension stirred at room temperature for 45 minutes. Bromine (11.1 mL, 216 mmol) was added dropwise over 5 minutes. The mixture was stirred at 100° C. for 3 hours and then cooled. Anhydrous methanol (35 mL) was added dropwise over 30 minutes, and then the reaction mixture was diluted with ether (400 mL), washed with 5% NaHCO$_3$ (800 mL), brine (200 mL), and then dried over MgSO$_4$. The mixture was filtered and concentrated in vacuo to afford material of sufficient purity (17) to use directly.

Procedure for preparing (3S)-3-benzyl-3,4-dihydro-2(1H)-quinoxalinone

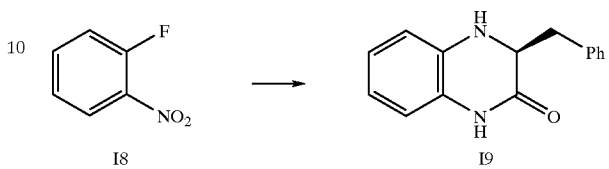

To ortho-fluoronitrobenzene (18) (6.5 g, 46 mmol) in ethanol (200 mL) and water (200 mL) under nitrogen was added L-phenylalanine (5.10 g, 31 mmol) and sodium bicarbonate (5.19 g, 62 mmol) and the suspension heated at reflux for 48 h. The red solution was coled, extracted with ether (2×50 mL—to remove any unreacted ortho-fluoronitrobenzene and concentrated to ½ volume. Pd/C (20%, 0.5 g) was added and a hydrogen balloon was attached. After stirring overnight the mixture was filtered, acidifed with 1N HCl to pH 4 and the solid that formed was collected. This was dried under high vacuum to afford the title compound (4.66 g, 53%) of sufficient purity (19) to use directly.

Procedure for preparing 3-benzyl-2(1H)-quinoxalinone

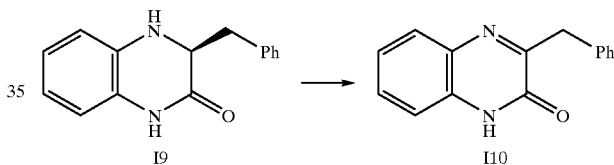

To (3S)-3-benzyl-3,4-dihydro-2(1H)-quinoxalinone (19) (4.66 g, 19.6 mmol) as a suspension in toluene (200 mL) was added DDQ (4.45 g, 1 equiv.) and the mixture stirred at room temperature overnight. The grey solid was collected by filtration and crystallized from ethanol/ water to afford the required compound (I10) (3.02 g, 65%).

$^1$H NMR (DMSO, 400 MHz): δ 12.35 (1H, s), 7.67 (1H, d, J=8.1 Hz), 7.44 (1H, t, J=7.8 Hz), 7.3–7.15 (7H, m), 4.08 (2H, s).

The invention compounds have demonstrated factor Xa, thrombin, and factor VIIa inhibitory activity in the standard assays commonly employed by those skilled in the art.

Determination of Factor Xa IC$_{50}$ and K$_i$ Constants

The ability of compounds to act as inhibitors of human factor Xa catalytic activity is assessed by determination of that concentration of test substance that inhibits by 50% (IC$_{50}$) the ability of human factor Xa to cleave the chromogenic substrate S2765 (N-CBz-D-Arg-L-Gly-L-Arg-p-nitroanilide. 2HCl, DiaPharma). Typically, 145 μL human factor Xa (1 nM final, Enzyme Research Laboratories) in 10 mM HEPES, 150 mM NaCl, 0.1% BSA, pH 7.4 (HBSA buffer), and 5 μL of test substance in DMSO (2% final) are incubated for 60 minutes at room temperature. Following preheating to 37° C. for 5 minutes, to this mixture is added 100 μL of S2765 in HBSA buffer. The velocity of S2765 hydrolysis is determined at 37° C. by measuring the initial rate of change of the optical density at OD$_{405}$ nM every 10 seconds for 5 minutes using a ThermoMax® Kinetic Microplate Reader.

For $K_i$ determinations, the assay conditions were essentially the same as above except for the following. The concentration of factor Xa was 50 pM, and that of the substrate, in this case a fluorogenic S2765 (i.e., S2765 with AMC tag instead of pNA, California Peptide Research), was over the range of 10 to 500 µM. The test compound and substrate in HBSA buffer were incubated as above, and the reaction was initiated with enzyme-buffer. The data (steady-state velocity at various concentrations of the substrate and the inhibitors) of the competitive inhibition was analyzed using the methods described by Segel (Enzyme Kinetics, Wiley Interscience Publications, 1993). A non-linear regression program, Kaleidograph and/or Microsoft Excel, was used to estimate the kinetic parameters ($K_m$, $V_{max}$, and $K_i$) by use of Michaelis-Menten and reciprocal Dixon plot fits.

Determination of Thrombin $IC_{50}$ and $K_i$ Constants

The ability of compounds to act as inhibitors of human thrombin catalytic activity is assessed by determination of that concentration of test substance that inhibits by 50% ($IC_{50}$) the ability of human thrombin to cleave the chromogenic substrate Chromozym TH (Tosyl-Gly-Pro-Arg-pNA*Ac, Boehringer Mannheim). Typically, 145 µL human thrombin (0.75 nM, Enzyme Research Laboratories) in a HPB buffer (10 mM HEPES, 100 mM NaCl, 0.05% BSA, 0.1% PEG-8000, pH 7.4) and 5 µL of test substance in DMSO (2% final) are incubated for 60 minutes at room temperature. Following preheating to 37° C. for 5 minutes, to this mixture is added 100 µL of Chromozym TH in HPB buffer. The velocity of Chromozym TH hydrolysis is determined at 37° C. by measuring the initial rate of change of the optical density at $OD_{405}$ nM every 10 seconds for 5 minutes using a ThermoMax® Kinetic Microplate Reader.

For $K_i$ determinations, the assay conditions were essentially the same as the aforementioned except for the following. The concentration of thrombin used was 50 pM, and that of a fluorogenic Chromozym TH (i.e., Chromozym TH with AMC instead of pNA tag, Novabiochem) was over the range of 1 to 40 µM. The test compound and substrate in HPB buffer were incubated as above, and the reaction was initiated with enzyme-buffer and run at 24° C. Kinetic analysis was performed as for factor Xa $K_i$ determinations.

Determination of Trypsin $IC_{50}$ and $K_i$ Constants

The ability of compounds to act as inhibitors of human trypsin catalytic activity is assessed by determination of that concentration of test substance that inhibits by 50% ($IC_{50}$) the ability of human trypsin to cleave the chromogenic substrate S2222 (N-Bz-L-Ile-L-Glu-L-Gly-L-Arg-p-nitroanilide. HCl, DiaPharma). Typically, 145 µL human trypsin (0.5 nM final) in 10 mM HEPES, 150 mM NaCl, 0.1% BSA, and 5 µL of the test substance in DMSO (2% final) are incubated for 60 minutes at room temperature. Following preheating to 37° C. for 5 minutes, to this mixture is added 100 µL of S2222 in HBSA buffer (100 µM final), and the velocity of S2222 hydrolysis is determined at 37° C. by measuring the optical density at $OD_{405}$ nM every 10 seconds over 5 minutes using a ThermoMax® Kinetic Microplate Reader.

For $K_i$ determinations, the assay conditions were essentially the same as the aforementioned except that the reaction was initiated with enzyme-buffer and run at 24° C. using a substrate range of 10 to 500 µM. Kinetic analysis was performed as for factor Xa $K_i$ determinations.

Determination of Tissue Factor/Factor VIIa $IC_{50}$

The ability of compounds to act as inhibitors of the catalytic activity of human tissue factor/factor VIIa complex is assessed by determination of that concentration of test substance that inhibits by 50% ($IC_{50}$ the ability of a complex of human recombinant tissue factor/factor VIIa to cleave the chromogenic substrate Spectrozyme VIIa ($CH_3SO_2$-D-CHA-Arg-pNA*AcOH, American Diagnostica). Typically, 50 µL human factor VIIa (Enzyme Research Laboratories) is incubated for 10 minutes as a 1:1 mixture (5 nM final each) with 95 µL recombinant human tissue factor (American Diagnostica) in a modified HBSA buffer (10 mM Hepes, 5 mM $CaCl_2$, 0.1% BSA, pH 8.0). Then, 5 µL of the test substance in DMSO (2% final) is added and incubated for 60 minutes at room temperature. Following preheating to 37° C. for 5 minutes, to this mixture is added 100 µL of Spectrozyme VIIa (500 µM final) in modified HBSA, and the velocity of Spectrozyme VIIa hydrolysis is determined at 37° C. by measuring the optical density at an $OD_{405}$ nM every 10 seconds over 5 minutes using a ThermoMax® Kinetic Microplate Reader.

In Vitro Assay for Human Prothrombinase

This assay demonstrates the ability of test compounds of the invention to inhibit the human prothrombinase (PTase) complex (typically comprising of human factor Va, human factor Xa, $Ca^{2+}$, and phospholipid moiety) and thereby the subsequent cleavage of prothrombin to yield thrombin. For determination of $IC_{50}$ (PTase) of the compounds of the invention, PTase activity was expressed by thrombin activity.

PTase reaction was performed in 100 µL of mixture containing PTase (20 µM) PCPS (Avanti Polar Lipids following a procedure modified from Barenholz et al., Biochemistry, 1977;16:2806–2810) in a 30:70 ratio, 2.5 nM human factor Va (Enzyme Research Laboratories), and 2.5 pM human factor Xa (Enzyme Research Laboratories) in modified HEPES buffer (10 mM Hepes, 150 mM NaCl, 0.1% PEG-8000, 0.05% BSA, 2.5 mM $CaCl_2$, pH 7.4), 3 µM human prothrombin (Enzyme Research Laboratories) and varied concentrations of the test compounds (1 nM to 100 µM in DMSO, 2% final). Reaction was started by co-incubating PTase with test compound for 60 minutes at room temperature, followed by addition of prothrombin for 6 minutes at room temperature. Next, the reaction was quenched by the addition of 100 µL of 20 mM EDTA. Activity of the thrombin (product) is then measured in the presence of 50 µL S2238 (250 µM final, H-D-Phe-Pip-Arg-pNA*Ac, DiaPharma) as substrate by measuring the change at 37° C. in $OD_{405}$ nM for 5 minutes at 10 second intervals using a ThermoMax® Kinetic Microplate Reader.

Example 2 in this assay has an IC50 of 0.0015 µM.

Determination of Prothrombin Time (PT)

Rat, rabbit, dog, and human blood (typically 1.8 mL) was collected and added to a sodium citrate solution (3.8%) to afford a 1:10 dilution. After centrifugation (2000 g for 10 minutes), the blood plasma was stored at −70° C. to 0° C. Conventional prothrombin time (PT) tests were carried out in the presence of various concentrations of test compound and the concentration of test compound required to double the clotting time determined. Typically, the test compound (50 µL volume of varying concentrations 0.1 µM to 1000 µM) and blood plasma (100 µL volume) were incubated at 37° C. for 10 minutes, and then tissue thromboplastin, typically Neoplastine from American Bioproducts, with calcium was added. Fibrin formation and the time required for a clot to form were determined using an automated ST4 Clot Detection System in duplicate.

In an ex-vivo modification of this assay, drug was administered intravenously or orally to a group of rats or rabbits. At various times blood samples were collected, and the PT coagulation assay as described above were performed.

Arterio-venous Shunt Stasis Antithrombotic Model

In vivo measurements of antithrombotic activity were performed according to the procedure of Vogel et al., Thromb. Res., 1989;54:399–410. Briefly, the vena cava was exposed, collateral veins were ligated, and sutures were loosely located around the inferior vena cava. These sutures were tightened after drug administration to induce stasis within the ligated portion of the vena cava. After an appropriate time, the thrombus was isolated and weighed. The effect of varying drug concentrations administered intravenously or orally on thrombus mass reflected antithrombotic activity.

Alternatively, and according to the procedure of Smith et al., *Br. J. Pharmacol.*, 1982;77:29–38, the left jugular and right carotid artery were exposed and cannulated. A shunt, which contains silk threads or preweighed cotton, is then inserted which connects the two cannulated vessels. Once drug has been administered, the shunt is closed, and the thrombus that forms on the foreign surface in the shunt is removed after a period of time. Clot weight then reflects antithrombotic activity.

Arterial Thrombosis Model $FeCl_3$ Induced Carotid Arterial Injury Model

The $FeCl_3$ induced injury to the carotid artery in rats was induced according to the method described by Kurz K. D., Main R. W., Sandusky G. E., *Thrombosis Research*, 1990;60:269–280 and Schumacher W. A. et al., *J. Pharmacology and Experimental Therapeutics*, 1993;267:1237–1242.

Male, Sprague-Dawley rats (375–410 g) were anesthetized with urethane (1500 mg\kg ip). Animals were laid on a 37° C. heating pad. The carotid artery was exposed through a midline cervical incision. Careful blunt dissection was used to isolate the vessel from the carotid sheath. Using forceps, the artery was lifted to provide sufficient clearance to insert two small pieces of polyethylene tubing (PE-205) underneath it. A temperature probe (Physitemp MT23/3) was placed between one of the pieces of tubing and the artery. Injury was induced by topical application on the carotid artery above the temperature probe of a small disc (3 mm dia.) of Whatman No. 1 filter paper previously dipped in a 35% solution of $FeCl_3$. The incision area was covered with aluminum foil in order to protect the $FeCl_3$ from degradation by light. The vessel temperature was monitored for 60 minutes after application of $FeCl_3$ as an indication of blood flow. Vessel temperature changes were recorded on a thermistor (Cole-Palmer Model 08533–41).

The time between the $FeCl_3$ application and the time at which the vessel temperature decreased abruptly (>2.4° C.) was recorded as the time to occlusion of the vessel. The fold shift in mean occlusion time (MOT), therefore, refers to the time to occlusion in drug-treated animal divided by control time to occlusion. Inhibitor compounds were given as an IV bolus (0.75 mg/kg) followed immediately by an IV infusion (50 μg/kg/min via femoral vein).

Typically, the compounds of the invention show 50% inhibition of factor Xa proteolytic activity on a synthetic substrate in concentrations ranging from 50 μM to 1 nM.

| Structure | Name | Thrombin $IC_{50}$ μM | Trypsin $IC_{50}$ μM | Xa $IC_{50}$ μM | VIIa % inhib. @ 100 μM |
|---|---|---|---|---|---|
| | 3-(4-5-[(2R,6S)-2,6-Dimethyl-tetrahydro-1(2H)-pyridinyl]pentyl-3-oxo-3,4-dihydro-2-quinoxalinyl)benzenecarboximidamide (Example 1) | 2.96 | 2.03 | 0.065 | 16 |
| | 3-(4-5-[(2R,6S)-2,6-dimethyl-tetrahydro-1(2H)-pyridinyl]pentyl-3-oxo-3,4-dihydro-2-quinoxalinyl)-4-hydroxybenzenecarboximidamide (Example 2) | 7.02 | 2.45 | 0.009 | 13 |

Further Biological Data of Example 2
In Vitro Diluted Prothrombin Time (dPT) Assay The effects of Example 2 on dPT were evaluated using pooled plasma from human volunteers. The compound concentration-dependently prolonged dPT and the concentrations which caused 2 fold prolongation of dPT for Example 2 was 0.05 $\mu$M, whereas at a concentration of 0.1 $\mu$M there was a 3.2 fold increase in dPT.

The effects of Example 2 on thrombosis and hemostasis has been studied in a rabbit veno-venous shunt model of thrombosis. In that model, a plastic shunt which contains cotton thread was inserted into abdominal vena cava and thrombus developed inside the shunt under control conditions. The end points of the experiment are the time to occlusion (TTO) and thrombus weight. Example 2 was given to the rabbit via jugular vein as a single bolus followed by constant infusion for 140 minutes. Three doses have been tested in a total of 15 rabbits (5 rabbits in each group): 30 $\mu$g/kg+1 $\mu$g/kg/min, 60 $\mu$g/kg+2 $\mu$g/kg/min, and 480 $\mu$g/kg+16 $\mu$g/kg/min. Example 2 dose-dependently prolonged the time to occlusion and reduced the net thrombus weight. In the highest dose group, TTO was increased from 17 minutes under control condition to 100 minutes. The net thrombus weight was reduced from 50 to 20 mg in that group. Example 2, at the highest dose, prolonged aPTT, PT, by 5-, and 3.9-fold, respectively.

The effects of Example 2 on thrombosis and hemostasis has been studied in a dog electrolytic injury model of thrombosis. In this model, the thrombosis influencing event is an electrical current is applied to the femoral vein (or artery) by applying an anodal direct current (300 uA) to the intimal surface of the vessel in the presence of restricted blood flow (Goldblatt clamps placed around the vessel). The end points of the experiment are the time to occlusion (TTO) and thrombus weight. Example 2 was given as a continuous infusion at rates of: 2.5 $\mu$g/kg/min, 5 $\mu$g/kg/min, and 10 $\mu$g/kg/min. which dose-dependently prolonged the time to occlusion and reduced the net thrombus weight. In the highest dose group, TTO was increased to near maximal effect of 240 minutes in both arteries and veins. The net thrombus weight was reduced from 50 mg to 18 mg [artery] and 110 mg to 15 mg [vein] in the highest dose group. Example 2, at the highest dose, prolonged aPTT, PT, by 1.4-, and 1.75-fold, respectively.

The foregoing biological tests have been used to establish the compounds of this invention are useful for preventing and treating thrombotic disorders, for example, venous thrombosis, deep vein thrombosis, thrombophlebitis, arterial embolism, coronary and cerebral arterial thrombosis, cerebral embolism, kidney embolism, pulmonary embolism, first or recurrent myocardial infarction, unstable angina, and cerebral infarction, stroke, atherosclerosis.

The compounds of the present invention can be administered alone or in combination with one or more therapeutic agents. These include, for example, other anticoagulant, antiplatelet, or platelet inhibitory agents which include non-steroidal anti-inflammatory agents such as aspirin, ibuprofen, naproxen sodium, indomethacin, piroxicam and ticlopidine, thrombin inhibitors such as argatroban, efegatran, inogatran, factor VIIa inhibitors, thrombolytic or fibrinolytic agents such as tissue plasminogen activator, urokinase or streptokinase, and GP IIIb-IIa antagonists.

The compounds are thus well-suited to formulation for convenient administration to mammals for the prevention and treatment of such disorders. The following examples further illustrate typical formulations provided by the invention.

| Formulation 1 | |
|---|---|
| Ingredient | Amount |
| Compound of Formulas I to V | 200 mg |
| Sodium benzoate | 5 mg |
| Isotonic saline | 1000 mL |

The above ingredients are mixed and dissolved in the saline for IV administration to a human suffering from, for example, arterial thrombosis.

| Formulation 2 | |
|---|---|
| Ingredient | Amount |
| Compound of Formulas I to V | 100 mg |
| Cellulose, microcrystalline | 400 mg |
| Stearic acid | 5 mg |
| Silicon dioxide | 10 mg |
| Sugar, confectionery | 50 mg |

The ingredients are blended to uniformity and pressed into a tablet that is well-suited for oral administration to a human for preventing, for example, cerebral infarction.

| Formulation 3 | |
|---|---|
| Ingredient | Amount |
| Compound of Formulas I to V | 200 mg |
| Starch, dried | 250 mg |
| Magnesium stearate | 10 mg |

The ingredients are combined and milled to afford material suitable for filling hard gelatin capsules administered to humans suffering from, for example, venous thrombosis.

| Formulation 4 | |
|---|---|
| Ingredient | Amount % wt./wt. |
| Compound of Formulas I to V | 1 |
| Polyethylene glycol 1000 | 74.5 |
| Polyethylene glycol 4000 | 24.5 |

The ingredients are combined via melting and then poured into molds containing 2.5 g total weight.

| Formulation 5 | |
|---|---|
| Ingredient | Amount % wt./wt. |
| Compound of Formulas I to V | 0.1% |
| Propellant 11/12 | 98.9% |
| Oleic acid | 1% |

The ingredients are dispersed in oleic acid with the propellant. The mixture is added to an aerosol container fitted with a metering device.

We claim:

1. A compound according to Formula I $$\text{(Formula I structure)}$$

I or stereoisomers or pharmaceutically acceptable salts, esters, or amides thereof, wherein:

A is selected from $NCH_2$, $N(alkyl)CH_2$, $CH_2N$, $CH_2N(alkyl)$;

B is selected from $(C_3\text{-}20)$alkyl, cycloalkyl, heteroalkyl, cycloalkylalkyl, heteroalkylalkyl, aryl, arylalkyl, heterocycle, heterocycloalkyl, each optionally substituted with R1 and R2;

D is selected from H, (C3–20)alkyl, cycloalkyl, heteroallkyl, cycloalkylalkyl, heteroalkylalkyl, aryl, arylalkyl, heterocycle, heterocycloalkyl, each optionally substituted with R1 and R2;

E is absent or selected from O;

F is N;

G is selected from alkyl, alkyl interrupted by one or more heteroatoms, cycloalkyl, cycloalkyl interrupted by one or more heteroatoms;

J is selected from aryl or heterocycle each optionally substituted with $R_1$ and $R_2$;

K is absent or selected from an alkyl, alkyl interrupted by one or more heteroatoms, cycloalkyl interrupted by one or more heteroatoms, cycloalkylalkyl interrupted by one or more heteroatoms, each optionally substituted with $R_1$ and $R_2$;

L is selected from H, chlorine, fluorine, bromine, iodine, OH, O(alkyl), amine, alkyl, fluoroalkyl, amide, $NO_2$, SH, $S(O)_n$(alkyl), $SO_3H$, $SO_3$alkyl, aldehyde, ketone, acid, ester, urea, Oalkylamide, Oalkylester, Oalkylacid, Nalkylacid, alkylamine, alkylamide, alkylketone, alkylacid, alkylester, alkylurea, Nalkylamide, Nalkylester, $NC(=O)$alkyl, $NC(=O)$aryl, $NC(=O)$cycloalkyl, $NC(=O)$cycloalkylalkyl, $NC(=O)$alkylaryl, $R_1$, $R_2$, nitrile;

$R_1$ is selected from H, amine, alkylamine, amide, $C(=NH)NHNH_2$, alkyl$C(=NH)NHNH_2$, $C(=NH)NHOH$, alkyl$C(=NH)NHOH$, $NHC(=NH)NH_2$, alkylNHC(=NH)$NH_2$, $C(=S)NH_2$, alkyl$C(=S)NH_2$, $C(=NH)$alkyl, alkyl$C(=NH)$alkyl, $C(=NR_3)N(R_4)(R_5)$, alkyl$C(=NR_3)N(R_4)(R_5)$;

$R_2$ is selected from H, chlorine, fluorine, bromine, iodine, OH, Oalkyl, amine, alkylaldehyde, alkylamide, alkylester, alkylketone, alkylacid, Oalkylamide, Oalkylacid, Oalkylester, aminealkylacid, aminealkylamide, aminealkylester, $NC(=O)$alkyl, $NC(=O)$aryl, $NC(=O)$cycloalkyl, $NC(=O)$alkylaryl, alkylamine, amide, aldehyde, ester, ketone, $NO_2$, SH, $S(O)_n(C_{1\text{-}10}$alkyl), $SO_3H$, $SO_3$alkyl, CHO, acid, alkyl, $C(=NH)$alkyl, $C(=NH)NHNH_2$, alkyl$C(=NH)NHNH_2$, $C(=NH)NHOH$, alkyl$C(=NH)NHOH$, $NHC(=NH)NH_2$, alkylNHC(=NH)$NH_2$, $C(=S)NH_2$, alkyl$C(=S)NH_2$, alkyl$C(=NH)$alkyl, $C(=NR_3)N(R_4)(R_5)$, alkyl$C(=NR_3)N(R_4)(R_5)$;

$R_3$, $R_4$ and $R_5$ are a hydrogen atom, alkyl group having 1 to 4 carbon atoms optionally interrupted by a heteroatom, or $R_4$ and $R_5$ are bonded to form $-(C_2)_p-W-(CH_2)_q-$, wherein p and q are an integer of 2 or 3, a certain position on the methylene chain is unsubstituted or substituted by an alkyl group having 1 to 4 carbon atoms, W is a direct bond, $-CH_2-$, $-O-$, $-N(R_6)-$, or $-S(O)_r-$ wherein $R_6$ is H or alkyl, and r is 0 or 1 or 2;

n is selected from 0, 1, 2;

$X_1$ is C;

$X_2$ is C;

$X_3$ is C;

$X_4$ is C; and

— represents an optional additional bond when A is N.

2. A compound according to claim 1 wherein the compound is according to Formula II $$\text{(Formula II structure)}$$

II or stereoisoiners or pharmaceutically acceptable salts, esters, or amides thereof, wherein A, B, E, G, J, K, and L are as defined above.

3. A pharmaceutical formulation comprising a compound of claim 1 admixed with a carrier, diluent, or excipient.

4. A pharmaceutical formulation comprising a compound of claim 2 together with a carrier, diluent, or excipient.

5. A method for inhibiting serine proteases comprising administering to a mammal an effective amount of serine protease inhibitor of claim 1.

6. A method according to claim 5, wherein said serine protease is factor Xa.

7. A method for the treatment or prophylaxis of thrombotic disorders in a mammal comprising administering to said mammal an effective amount of a compound according to claim 1.

8. A method according to claim 7, wherein said disorder is venous thrombosis.

9. A method according to claim 7, wherein said disorder is arterial thrombosis.

10. A method according to claim 7, wherein said disorder is pulmonary embolism.

11. A method according to claim 7, wherein said disorder is myocardial infarction.

12. A method according to claim 7, wherein said disorder is cerebral infarction.

13. A method according to claim 7, wherein said disorder is restenosis.

14. A method according to claim 7, wherein said disorder is cancer.

15. A method according to claim 7, wherein said disorder is angina.

16. A method according to claim 7, wherein said disorder is diabetes.

17. A method according to claim 7, wherein said disorder is heart failure.

18. A method according to claim 7, wherein said disorder is atrial fibrillation.

* * * * *